United States Patent
Yanagi et al.

(10) Patent No.: US 12,378,597 B2
(45) Date of Patent: Aug. 5, 2025

(54) PROBE, PROBE SET, AND METHOD FOR IDENTIFYING DESIRED DNA SEQUENCE IN SOLUTION

(71) Applicant: HITACHI, LTD., Tokyo (JP)

(72) Inventors: Itaru Yanagi, Tokyo (JP); Takahide Yokoi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 403 days.

(21) Appl. No.: 17/109,493

(22) Filed: Dec. 2, 2020

(65) Prior Publication Data
US 2021/0189467 A1    Jun. 24, 2021

(30) Foreign Application Priority Data
Dec. 19, 2019    (JP) .................................. 2019-229019

(51) Int. Cl.
*C12Q 1/6816* (2018.01)
*G01N 27/447* (2006.01)
*G01N 33/487* (2006.01)

(52) U.S. Cl.
CPC ..... *C12Q 1/6816* (2013.01); *G01N 27/44791* (2013.01); *G01N 33/48721* (2013.01)

(58) Field of Classification Search
CPC ............ C12Q 1/6869; C12Q 2565/631; C12Q 2563/131; C12Q 2525/107; C12Q 1/6825; C12Q 2525/161; C12Q 2563/119; C12Q 2563/155; C12Q 2565/133
See application file for complete search history.

(56) References Cited

U.S. PATENT DOCUMENTS

| | | | |
|---|---|---|---|
| 6,316,230 B1 * | 11/2001 | Egholm | C12Q 1/6853 536/25.32 |
| 6,723,513 B2 * | 4/2004 | Lexow | C12Q 1/6806 435/6.12 |
| 9,914,966 B1 | 3/2018 | Dimitrov et al. | |
| 2003/0013091 A1 | 1/2003 | Dimitrov | |
| 2005/0136408 A1 * | 6/2005 | Tom-Moy | C12Q 1/6816 435/6.12 |
| 2006/0063196 A1 | 3/2006 | Akeson et al. | |
| 2009/0035777 A1 | 2/2009 | Kokoris et al. | |
| 2010/0015607 A1 | 1/2010 | Geiss et al. | |

(Continued)

FOREIGN PATENT DOCUMENTS

| | | |
|---|---|---|
| EP | 2171088 A2 | 4/2010 |
| JP | 2004-537301 A | 12/2004 |

(Continued)

OTHER PUBLICATIONS

Misra et al. Biochemistry. 1998. 37:1917-1925. (Year: 1998).*
Orum et al. Nucleic Acids Research. 1993. 21(23):5332-5336. (Year: 1993).*
Fouz et al. Molecules. 2020. 25(4):786. (Year: 2020).*
Morin et al. PLOS ONE. 2016. 11(5):e0154426, 21 pages. (Year: 2016).*

(Continued)

*Primary Examiner* — Joseph G. Dauner
(74) *Attorney, Agent, or Firm* — PROCOPIO, CORY, HARGREAVES & SAVITCH LEP

(57) ABSTRACT

The present disclosure proposes a probe including a sequence recognition portion that is capable of specifically binding to a desired DNA sequence, and a first probe portion that includes a plurality of 3-dimensional structures arranged downstream from an end of the sequence recognition portion, in which the plurality of 3-dimensional structures are arranged in an order so that the order corresponds one-to-one with the DNA sequence.

5 Claims, 19 Drawing Sheets

(56) References Cited

U.S. PATENT DOCUMENTS

| | | | |
|---|---|---|---|
| 2011/0223596 A1* | 9/2011 | Woudenberg | C12Q 1/6827 435/6.1 |
| 2013/0281306 A1* | 10/2013 | Rigatti | C12Q 1/6874 506/2 |
| 2016/0002704 A1* | 1/2016 | Diehl | C12Q 1/6841 506/9 |
| 2017/0074855 A1 | 3/2017 | Morin et al. | |
| 2017/0101676 A1* | 4/2017 | Teng | C12Q 1/6869 |
| 2018/0023115 A1 | 1/2018 | Morin et al. | |
| 2018/0155768 A1* | 6/2018 | Cohen | C12Q 1/6825 |
| 2018/0314791 A1* | 11/2018 | Gross | G16B 50/50 |
| 2018/0363035 A1 | 12/2018 | Morin et al. | |
| 2019/0062814 A1 | 2/2019 | Aksimentiev et al. | |

FOREIGN PATENT DOCUMENTS

| | | | |
|---|---|---|---|
| JP | 2009-521230 A | 6/2009 | |
| JP | 2010-530759 A | 9/2010 | |
| JP | 2018-505414 A | 2/2018 | |
| WO | 2008/157696 A2 | 12/2008 | |
| WO | 2012/003330 A2 | 1/2012 | |
| WO | 2014/144217 A1 | 9/2014 | |
| WO | WO-2014205266 A2 * | 12/2014 | A61K 31/135 |
| WO | 2018/093976 A1 | 5/2018 | |
| WO | WO-2018089550 A1 * | 5/2018 | C12N 15/1096 |

OTHER PUBLICATIONS

Rosenstein, J. et al. "Integrated nanopore sensing platform with sub-microsecond temporal resolution" in Nature Methods, May 2012, pp. 487-494, vol. 9, No. 5.

Kwok, H. et al. "Nanopore Fabrication by Controlled Dielectric Breakdown" in PLoS One, May 2014, vol. 9, No. 3 (6 pages).

Briggs, K. et al. "Kinetics of nanopore fabrication during controlled breakdown of dielectric membranes in solution" in Nanotechnology, Feb. 4, 2015, vol. 26 (11 pages).

Briggs, K. et al. "Automated Fabrication of 2-nm Solid-State Nanopores for Nucleic Acid Analysis" Small Journal, 2014 (10 pages).

Morin, T. et al. "Nanopore-Based Target Sequence Detection" in PLoS One, May 5, 2016, vol. 11, No. 5 (21 pages).

Yanagi, I. et al. "Two-step breakdown of a SiN membrane for nanopore fabrication: Formation of thin portion and penetration" in Nature: Scientific Reports, Jul. 4, 2018 (13 pages).

Extended European Search Report for related European Patent Application No. 20210318.0, mailed on May 14, 2021 in 8 pages.

Office Action received in corresponding Japanese Patent Application No. 2019-229019, dated Mar. 14, 2023, in 5 pages.

Yanagi, Itaru, et al., "Stable fabrication of a large nanopore by controlled dielectric breakdown in a high-pH solution for the detection of various-sized molecules", Scientific Reports, (2019) 9:13143, https://doi.org/10.1038/s41598-019-49622-y, published online Sep. 11, 2019, in 15 pages.

* cited by examiner (f)

(g)

(f)

(g)

(a)

(b)

PROBE, PROBE SET, AND METHOD FOR IDENTIFYING DESIRED DNA SEQUENCE IN SOLUTION

BACKGROUND OF THE INVENTION

1. Field of the Invention

The present disclosure relates to a probe, a probe set and a method for identifying a desired DNA sequence in a solution.

2. Description of the Related Art

As a means for detecting a molecule or a particle present in an aqueous solution, a technique utilizing nanopores has been investigated. The technique intends to detect passage of a detection target substance or to determine structural characteristics of the detection target substance by measuring time-dependent changes in ionic current that flows between electrodes as follows: providing pores (nanopores) having a size that is almost the same as that of a detection target molecule or particle on a membrane, filling chambers above and below the membrane with an aqueous solution, providing electrodes in both the chambers so that the electrodes are each come into contact with the aqueous solution, introducing a detection target substance as a target for the measurement in one of the chambers to give a potential difference between the electrodes provided in both the chambers so that the detection target substance is electrophoresed to pass through the nanopores, and then measuring the time-dependent change in ionic current that flows between the electrodes. In general, when a detection target substance passes through a nanopore, the detection target substance blocks a part of the nanopore. Thus, electrical resistance increases, and therefore ionic current decreases. The electrical resistance further increases as the size of the detection target substance becomes larger. As a result, the ionic current further decreases.

In production of a nanopore device, production methods using a semiconductor substrate, a semiconductor material, and a semiconductor process are attracting attention from the standpoint of high mechanical strength or the like. For example, a membrane can be formed by using a silicon nitride film (SiNx film), and nanopores each having a pore diameter of 10 nm or less can be formed as follows: using, for example, a transmission electron microscope (TEM), concentrating electron beams in a small irradiation area on the membrane, and controlling energy and electric current of the beams to form the nanopores (Jacob K Rosenstein, et al., Nature Methods, Vol. 9, No. 5, 487-492 (2012)). In addition, recently, new methods for producing nanopores utilizing a dielectric breakdown phenomenon of a membrane as described in Harold Kwok, et al., PloS ONE, Vol. 9, No. 3, e92880 (2013), Kyle Briggs, et al., Nanotechnology, Vol. 26, 084004 (2015), and Kyle Briggs, et al., Small, 10(10):2077-86 (2014) have been reported.

An application of the measurement utilizing nanopores includes, for example, detection and counting of the number of specific target substances in an aqueous solution. For example, when a specific target substance is present in an aqueous solution, by allowing a large molecule that can be adsorbed only on the specific target substance to bind to the specific target substance, the extent of decrease in ionic current that occurs when the specific target substance passes through the nanopores is increased. Thus, it becomes possible to distinguish the decrease in ionic current based on a decrease in ionic current that occurs when a non-specific target substance passes through the nanopores. As a result, identification of a specific target substance in an aqueous solution and counting of the number of the specific target substance by nanopore measurement become possible. If there is no specific target substance in an aqueous solution, only a small decrease in ionic current due to a non-specific target substance that passes through nanopores is observed. From this information, it is possible to make a decision that the specific target substance is not present in the aqueous solution. Herein, the specific target substance refers to, for example, DNA containing a specific sequence.

As an example, a method in Trevor J. Morin, et al., PLoS ONE 11(5):e0154426. doi:10.1371/journal.pone.0154426 is described below. In this example, a structure in which PEG is bound to PNA (hereinafter, referred to as a "PNA-PEG probe") is used. The PNA portion of the PNA-PEG probe is designed so as to specifically bind to only a specific sequence portion of DNA having the specific sequence. Further, the probe is designed such that the size of the PEG is large and there is a difference between a decrease in ionic current when the DNA having the specific sequence to which the PNA-PEG probe is bound passes through a nanopore and a decrease in ionic current when DNA to which the PNA-PEG probe is not bound (DNA not containing the specific sequence) passes through the nanopore. Thus, it becomes possible to identify the DNA having the specific sequence present in an aqueous solution, to count the number of the DNA having the specific sequence, and to verify whether the DNA having the specific sequence is present or not.

When two or more types, for example, n types (n is an integer of two or more) of detection target specific DNA sequences are present, the method includes providing n types of probes having sizes that are different from each other and each having capability to specifically bind to each of the specific DNA sequences, and allowing each of the probes to specifically bind to each of the specific DNA sequences. The method further includes allowing each of the specific DNA sequences bound to each of the probes to pass through a nanopore. Then, the extent of decrease in ionic current when each of the specific DNA sequences bound to each of the probes passes through the nanopore varies depending on the size of the probe. Thus, it becomes possible to identify each of the specific DNA sequences, to count the number of each of the specific DNA sequences, and to verify whether each of the specific DNA sequences is present or not.

Actually, FIGS. 4A to 4C in US 2018/0363035 A1 describes a method including allowing probes having different sizes to bind to DNA, and identifying which size of probe is bound to DNA that has passed through a nanopore based on difference in extent of decrease in ionic current when the probe-DNA conjugate material passes through the nanopore. US 2019/0062814 A1 also discloses related art.

SUMMARY OF THE INVENTION

When two or more types, for example, n types (n is an integer of two or more) of detection target specific DNA sequences are present, it is theoretically possible to identify each of the specific DNA sequences and count the number of each of the specific DNA sequences, and verify whether each of the specific DNA sequences is present or not by providing n types of probes having sizes that are different from each other and each having capability to specifically bind to each of the specific DNA sequences, allowing each of the probes to specifically bind to each of the specific DNA sequences, and measuring decrease in ionic current when each of the specific DNA sequences with each of the probes passes through a nanopore.

However, it is impossible to increase the number of n (increase the types of specific DNA sequences) unlimitedly (i.e., unlimited types cannot be used). As reported in Jacob K Rosenstein, et al., Nature Methods, Vol. 9, No. 5, 487-492 (2012), Harold Kwok, et al., PloS ONE, Vol. 9, No. 3, e92880 (2013), Kyle Briggs, et al., Nanotechnology, Vol. 26, 084004 (2015), Kyle Briggs, et al., Small, 10(10):2077-86 (2014), Kyle Briggs, et al., Small, 10(10):2077-86 (2014), Trevor J. Morin, et al., PLoS ONE 11(5):e0154426. doi: 10.1371/journal. pone. 0154426, Itaru Yanagi, et al., Scientific Report, 8, 10129 (2018), and other numerous documents, it is known that when a single molecule (one type of molecule) repeatedly passes through a nanopore, decreases in ionic current ($\Delta I$) vary and are not identical with each other. This deviation reflects the following differences: whether the molecule passes around the center or near the periphery of the nanopore when the molecule passes through the nanopore; difference of the angle at which the molecule enters the nanopore; and difference of the direction of the molecule in the nanopore. Thus the extent of decrease in ionic current $\Delta I$, when a certain molecule passes through a nanopore, with deviation can be represented by $\Delta I = \Delta I_{ave.} \pm \Delta I_{dev.}$. ($\Delta I_{ave.}$ is the average of decreases in ionic current in a plurality of measurements, and $\Delta I_{dev.}$ is a deviation in the decreases in ionic current in the measurements).

When there are small differences in size among the probes, each of which binds to each of different specific DNA sequences to be detected, difference in $\Delta I_{ave.}$ value obtained when the different specific DNA sequences each bound to each of the probes pass through a nanopore becomes small. In this case, as described above, since $\Delta I$ has a deviation $\Delta I_{dev.}$ even when different specific DNA sequences each having a different type (different size) of probe pass through the nanopore, almost the same $\Delta I$ value is often observed. As a result, misidentification of a specific DNA sequence tends to occur, which leads to decrease in accuracy in identification or counting of the number of the specific DNA sequence, or decrease in accuracy in verification of whether the specific DNA sequence is present or not.

Thus, to increase accuracy in identification or accuracy in detection of a specific DNA sequence, the difference in size among the probes is desired to be as large as possible. On the other hand, of course, a construct (DNA contruct) that is larger than the size of the nanopore cannot enter the nanopore. Therefore, it is required to provide probes having a plurality of sizes that are smaller than the size of the nanopore. Thus, the number of types of specific DNA sequences that can be identified with high accuracy or detected with high accuracy in counting of the number of the specific DNA sequences is naturally limited.

For example, four types of different-sized probes are provided for the purpose of detecting specific DNA sequences a, b, c, and d, and these probes are bound to the respective DNA sequences a, b, c, and d to form conjugates. Then, $\Delta I$ is measured when each of the resulting conjugates passes through a nanopore. When $\Delta I$ values obtained with respect to the conjugates satisfy $\Delta Ia=1.5x \pm x$, $\Delta Ib=4x \pm x$, $\Delta Ic=76x \pm x$, and $\Delta Id=10x \pm x$, respectively, since the $\Delta I$ values are separated from each other even including deviations, the specific DNA sequences a, b, c, and d that have passed through the nanopore can be identified accurately from the $\Delta I$ values.

Further, the following is assumed as an example: when there is no substance that prevents ionic current in a nanopore, the value of ionic current that flows in the nanopore (hereinafter, referred to as a "baseline electric current value") is about 11x, and the size of a probe that is bound to a specific DNA sequence d is almost the same as the size of the nanopore. Then, a case in which one DNA sequence to be detected is added, and specific DNA sequences a, b, c, d, and e are detected will be considered. Then, five types of probes having different sizes are provided. The five probes are bound to specific DNA sequences a, b, c, d, and e, respectively, and the resulting conjugates pass through a nanopore. Then, $\Delta I$ is measured when each of the conjugates passes through the nanopore. When $\Delta I$ values including deviations obtained with respect to the conjugates are represented by $\Delta Ia=1.5x \pm x$, $\Delta Ib=4x \pm x$, $\Delta Ic=7x \pm x$, $\Delta Id=10x \pm x$, and $\Delta Ie=8.5x \pm x$, respectively, the values of $\Delta Ic$, $\Delta Id$, and $\Delta Ie$ partly overlap each other in consideration of the deviations. In this case, accuracy in identification of the specific DNA sequences c, d, and e decreases. That is, as the number of types of specific DNA sequences to be detected increases, accuracy in identification of each of the DNA sequences decreases.

Harold Kwok, et al., PloS ONE, Vol. 9, No. 3, e92880 (2013) discloses another method for identifying a plurality of specific DNA sequences in an aqueous solution using a nanopore. In Harold Kwok, et al., PloS ONE, Vol. 9, No. 3, e92880 (2013), a probe called an NANP is used. The NANP is a molecule formed from a large construct and a plurality of sequence recognition portions that are bound to the construct. The sequence recognition portions can recognize and bind to specific DNA sequences. In Harold Kwok, et al., PloS ONE, Vol. 9, No. 3, e92880. (2013), a detection target specific DNA sequence is called a biomarker. A plurality of biomarkers are identified by using a nanopore as follows. As described in FIG. 10 in Harold Kwok, et al., PloS ONE, Vol. 9, No. 3, e92880. (2013), NANPs are suitably designed so that a construct in which detection target biomarkers (four types are used in FIG. 10) and NANPs having different sizes (five types are used in FIG. 10) are conjugated alternately is formed. Thereafter, the construct formed is passed through a nanopore, and ionic current that is produced when the construct passes through the nanopore is measured. Then, from the manner of change in the ionic current that occurs due to the difference in size of the NANPs (a conceptual image is shown in FIG. 10), types of the biomarkers in the construct formed can be identified. In this method, there is a problem that is the same as in the above-described methods. That is, as the number of types of NANPs increases, the difference in $\Delta I$ derived from each of the NANPs decreases, which results in decreased accuracy in identification of each of the biomarkers. Actually, in the method, to detect n types of biomarkers (DNA sequences) having different sizes, n+1 types of NANPs (probes) having different sizes are required. That is, the method requires a greater number of different-sized probes than the above-described method (the method using n types of probes to detect n types of DNA sequences). Therefore, it is thought that accuracy in identification of a specific DNA sequence is lower than that in the above-described method.

The present disclosure provides, in view of the above circumstances, a technique for identifying a specific DNA sequence and counting of the number of the specific DNA sequence, or verifying whether the specific DNA sequence is present or not, in which it is possible to maintain a high accuracy in identification of the specific DNA sequence and counting of the number of the specific DNA sequence, or a high accuracy in verification of whether the specific DNA sequence is present or not, even when the number of types of specific DNA sequences to be detected increases.

To solve the above problem, the present disclosure proposes a probe including a sequence recognition portion that is capable of specifically binding to a desired DNA sequence, and a first probe portion that includes a plurality of 3-dimensional structures arranged downstream from an end of the sequence recognition portion, wherein the plurality of 3-dimensional structures are arranged in an order so that the order corresponds one-to-one with the DNA sequence.

In addition, the present disclosure proposes a method for identification of a desired DNA sequence in a solution, the method including allowing the above-described probe to bind to the DNA sequence at a sequence recognition portion of the probe, measuring electric current when the resulting construct in which the probe and the DNA sequence are bound to each other passes through a nanopore, and specifying the order of a plurality of 3-dimensional structures arranged based on a wave form of the electric current to identify the presence of the DNA sequence, wherein the wave form of the electric current is a signal that reflects passage of the plurality of constructs.

Further characteristics concerning the present disclosure will become apparent from contents of the present specification and drawings attached hereto. Embodiments of the present disclosure will be achieved and accomplished by an element and combinations of various elements, and embodiments in the following detailed description and claims attached hereto.

It should be noted that the contents of the present specification are for illustrative purpose only, and are not intended to limit the scope of the claimed invention or application examples in the present disclosure in any way.

According to the present disclosure, a detection target specific DNA sequence can be identified and counted with high accuracy by measurement using a nanopore.

DESCRIPTION OF THE PREFERRED EMBODIMENTS

In all figures for describing the present embodiments, a constituent having the same function will be denoted by the same sign, and repeated descriptions are eliminated as much as possible. Hereinafter, the present embodiments are described in detail with reference to drawings. Device structures and materials shown in Examples are examples for realizing the concept of the present invention, and materials and dimensions are not strictly limited thereto. In addition, specific voltage values, electric current values, voltage application time, and the like shown in Examples are examples for realizing the concept of the present invention, and voltage values, electric current values, and are not intended to be limiting.

The present embodiments consider, as an example, a situation in which a plurality of specific DNA sequences to be detected are each individually present in a different DNA fragment so that a single specific DNA sequence is contained in each DNA fragment. That is, a situation in which a plurality of specific DNA sequences are contained in a single DNA fragment, and the plurality of specific DNA sequences in the single DNA fragment are identified by nanopore measurement is not discussed. In a DNA sample pre-treatment step performed in advance, it is possible, by using a known method, to prepare a sample such that only one of the plurality of specific DNA sequences to be detected is individually contained in each different DNA fragment.

(1) First Embodiment

<Example of Constitution of Bioanalyzer>

Figure 1:
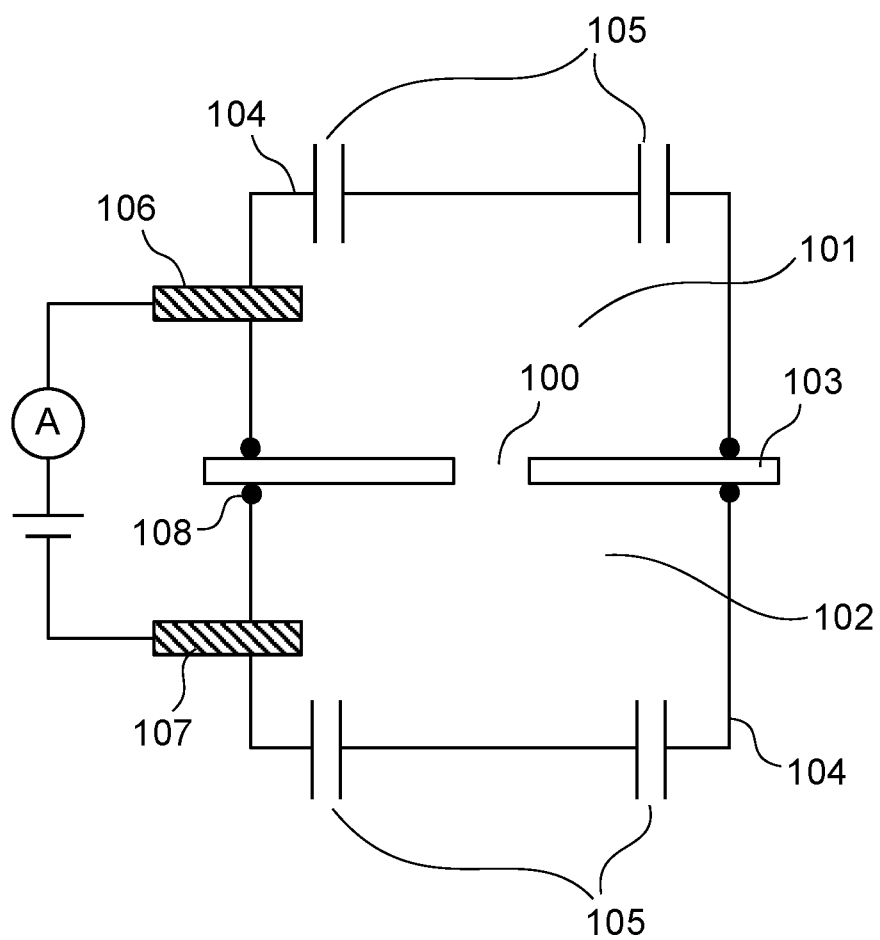
FIG. 1 is a schematic diagram of a system for measuring electric current that flows through a nanopore.

FIG. 1 is a schematic diagram showing a setup (example of constitution of a bioanalyzer) for measuring ionic current that flows through a nanopore. The sign 100 denotes a nanopore, and signs 101 and 102 denote solutions. When a target substance that passes through the nanopore 100 is measured, the measurement target substance is contained in any one of or both of the solutions 101 and 102. As solutions 101 and 102, for example, an aqueous solution of KCl can be used. The sign 103 denotes a membrane having the nanopore 100. As a material of the membrane, for example, SiN can be used. The sign 104 denotes a chamber that accommodates the solution. The chambers 104 are disposed above and below the membrane 103. The chambers 104 and the membrane 103 are connected with each other via an O-ring 108. The sign 105 denotes a solution inlet for introducing the solution into the chamber and a solution outlet. The signs 106 and 107 denote electrodes that are in contact with the solution. For example, a Ag/AgCl electrode can be used as the electrode. When a potential difference is established between the electrodes 106 and 107, ions in the solution pass through the nanopore 100 and ionic current flows. This electric current is measured by an ammeter that is connected between the electrodes 106 and 107. The electric current value changes when the measurement target substance passes through the nanopore. Generally, when the measurement target substance passes through the nanopore, the measurement target substance acts as a resistor that electrically blocks a part of the nanopore, and therefore the electric current decreases. Major examples of the measurement target substance as described herein are DNA and probe-conjugated DNA.

<Example of Probe Including Specific DNA Sequence and Sequence Recognition Portion (Before Conjugation)>

Figure 2:
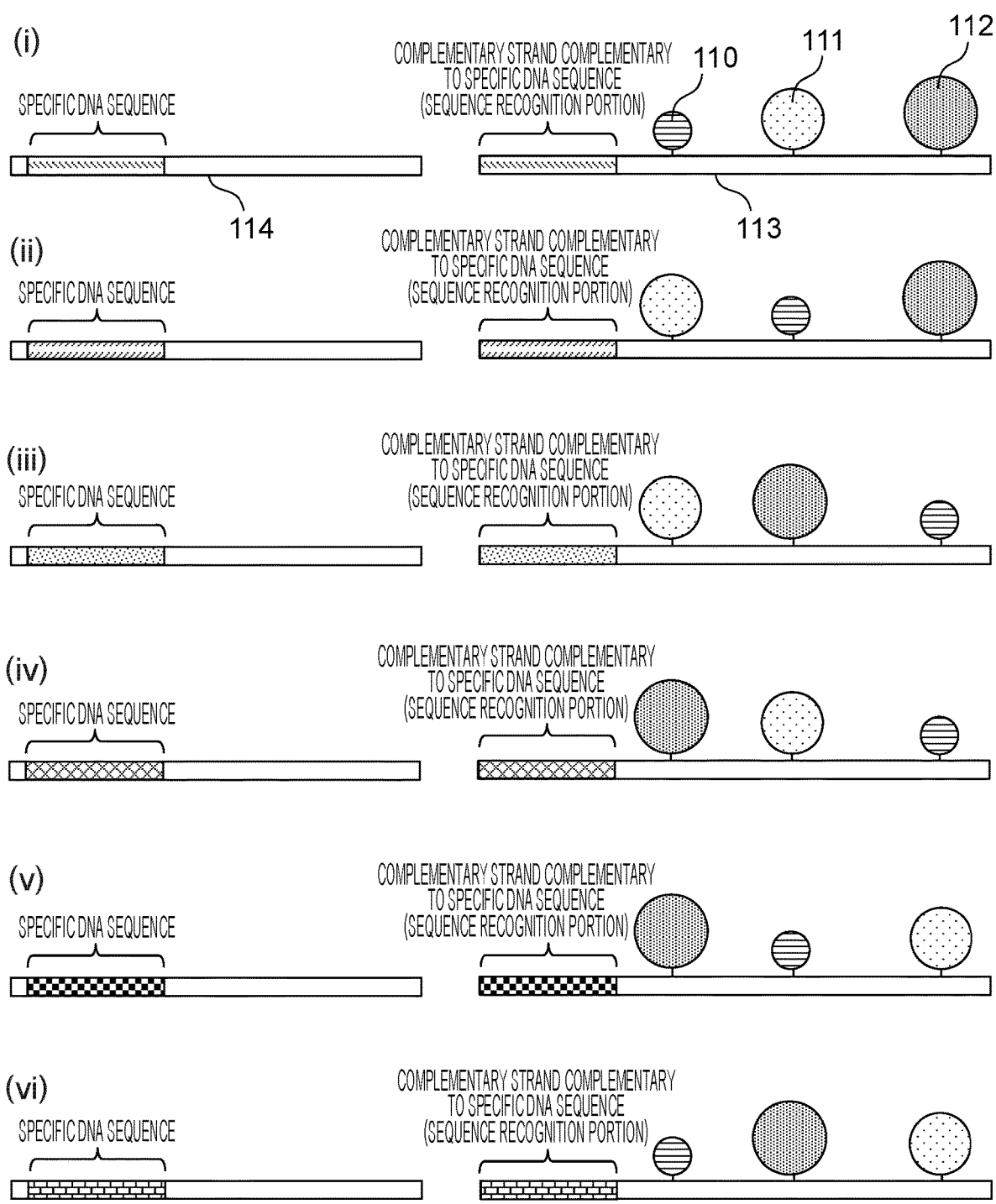
FIG. 2 shows illustrations showing structures of various DNA fragments each having a specific DNA sequence to be detected (six types of DNA fragments shown on the left side of the illustration, which are representatively denoted by "114"), and probes each including a sequence recognition portion that can specifically recognize and bind to the specific DNA sequence portion (six types of probes shown on the right side of the illustration, which are representatively denoted by "113")

FIG. 2 shows illustrations showing structures of various DNA fragments each having a specific DNA sequence to be detected (six types of DNA fragments shown on the left side of the illustration, which are representatively denoted by "114"), and probes each including a sequence recognition portion that can specifically recognize and bind to the specific DNA sequence portion (six types of probes shown on the right side of the illustration, which are representatively denoted by "113"). In the figure, 6 types of DNA fragments and probes are shown as examples. However, the number of types of the DNA fragments and probes may vary depending on the number of types of DNA sequences to be detected.

A characteristic of this embodiment is that each probe has an arrangement including a plurality of different-sized 3-dimensional structures downstream from an end of the sequence recognition portion. In the figure, probes in which three 3-dimensional structures 110, 111, and 112 are arranged are shown as an example. In the six types of probes, the characteristic is that the arrangements of the 3-dimensional structures are different from each other. As the sequence recognition portion, it is preferred to use, for example, a complementary strand sequence that can specifically bind to a specific DNA sequence.

<Example of Probe Including Specific DNA Sequence and Sequence Recognition Portion (After Conjugation)>

Figure 3:
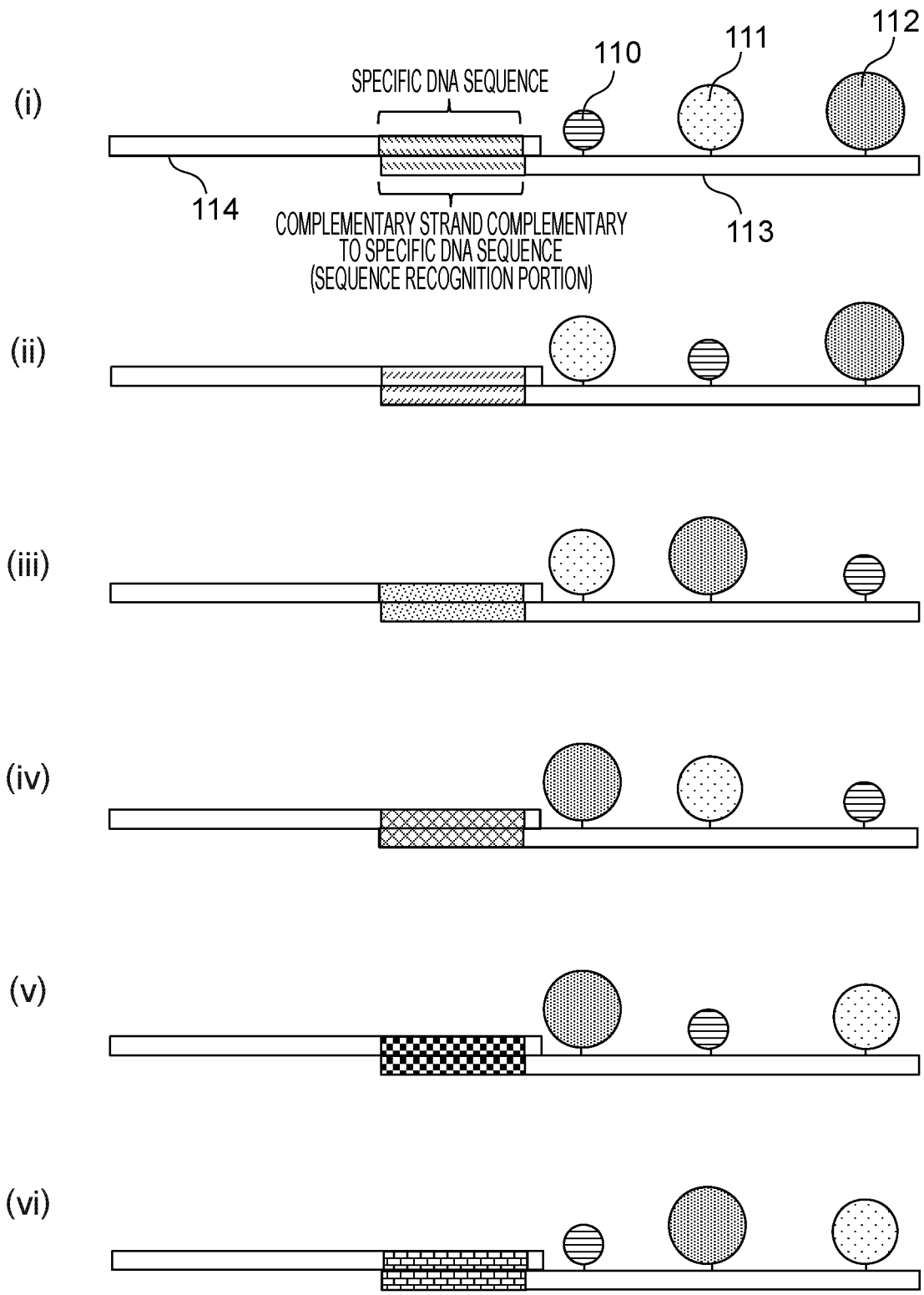
FIG. 3 shows illustrations showing structural examples in which various DNA fragments each having a specific DNA sequence, and probes each including a sequence recognition portion that can specifically recognize and bind to a specific DNA sequence portion as shown in FIG. 2 have been bound to each other.

FIG. 3 shows illustrations showing structural examples in which various DNA fragments each having a specific DNA sequence, and probes each including a sequence recognition portion that can specifically recognize and bind to a specific DNA sequence portion as shown in FIG. 2 have been bound to each other. The detection target DNA fragment having a specific DNA sequence and the probe including a sequence recognition portion that can specifically recognize and bind to the specific DNA sequence portion can be bound to each other by mixing them in an aqueous solution.

<Change in Electric Current Value Concerning Each Probe-Conjugated DNA Fragment>

Figure 4:
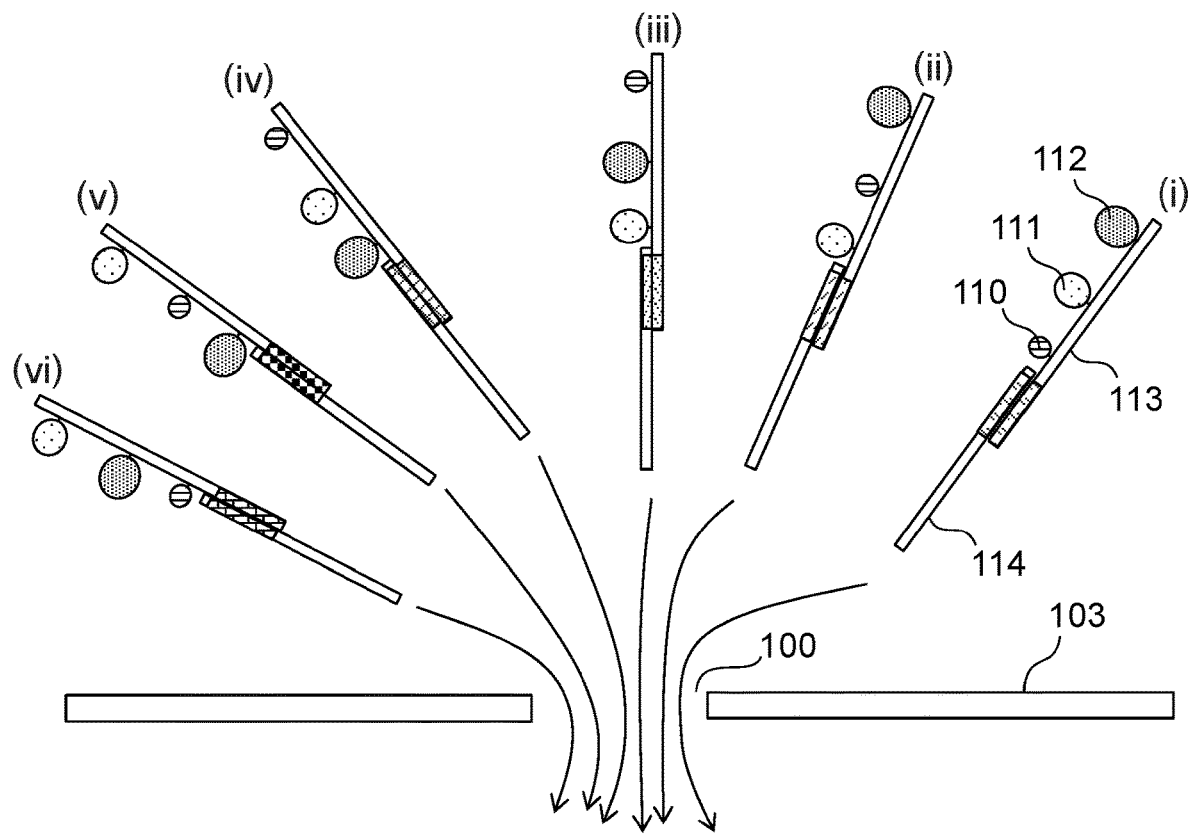
FIG. 4 shows a diagram showing DNA fragments each having a specific DNA sequence to which each of the six types of different probes is bound passing through a nanopore, and graphs each showing change in electric current that occurs when each of the DNA fragments passes through the nanopore.
Figure 4:
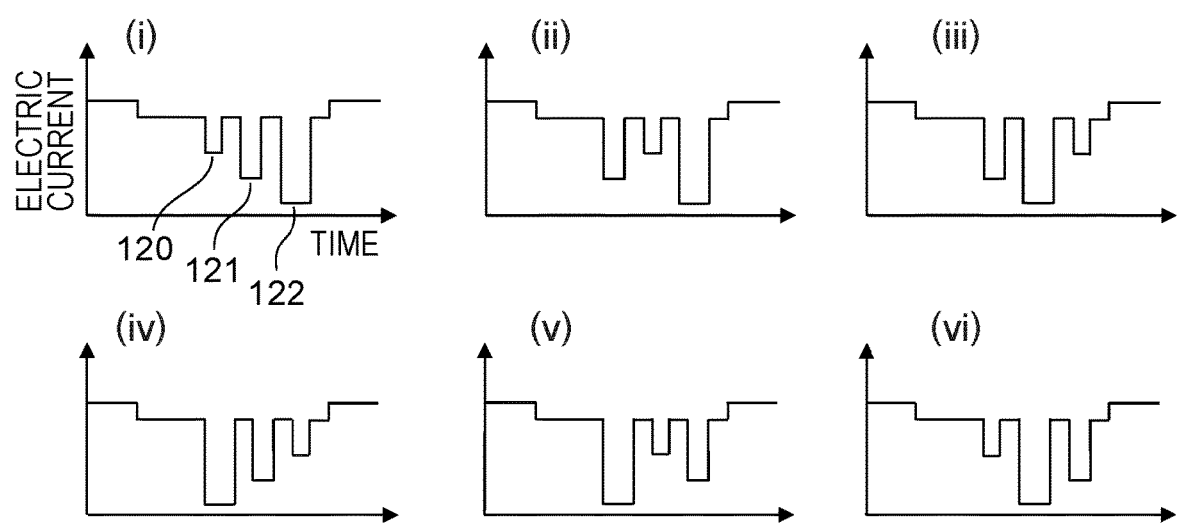

FIG. 4 shows a diagram showing DNA fragments each having a specific DNA sequence to which each of the six types of different probes is bound passing through a nanopore 100, and graphs each showing change in electric current value that occurs when each of the DNA fragments passes through the nanopore 100.

For example, in a case of FIG. 4 (i), at the time when an end of the DNA fragment enters the nanopore 100, electric current value that flows through the nanopore 100 decreases to a small extent, and at the time when the 3-dimensional structure 110 part enters the nanopore 100, the electric current value further decreases (as indicated by 120). Thereafter, when the 3-dimensional structure 110 has passed through the nanopore, the electric current value almost returns to a level around the value before the 3-dimensional structure 110 enters the nanopore 100. Next, at the time when the 3-dimensional structure 111 enters the nanopore, the electric current value decreases again (as indicated by 121). In this case, since the 3-dimensional structure 111 is larger than the 3-dimensional structure 110, the extent of decrease in electric current when the 3-dimensional structure 111 enters the nanopore 100 is larger than the extent of decrease in electric current when the 3-dimensional structure 110 enters the nanopore 100. When the 3-dimensional structure 111 has passed through the nanopore 100, the electric current value almost returns to a level around the value before the 3-dimensional structure 111 enters the nanopore 100. Thereafter, at the time when the 3-dimensional structure 112 enters the nanopore 100, the electric current value decreases again (as indicated by 122). In this case, since the 3-dimensional structure 112 is larger than the 3-dimensional structure 111, the extent of decrease in electric current when the 3-dimensional structure 112 enters the nanopore 100 is larger than the extent of decrease in electric current when the 3-dimensional structure 111 enters the nanopore 100. Then, when the 3-dimensional structure 112 has passed through the nanopore 100, the electric current value almost returns to a level around the value before the 3-dimensional structure 112 enters the nanopore 100. When the conjugate in which the probe 113 and the DNA fragment having a specific DNA sequence 114 are bound to each other has passed through the nanopore 100, the electric current value returns to the value of electric current that flows at the time when there is no target substance in the nanopore 100.

As described above, from the order of observed block signals having different levels (120, 121, and 122) that are each generated when each of the 3-dimensional structures passes through the nanopore, information concerning order of the different-sized 3-dimensional structures arranged in the probe 113 can be obtained. The same applies to FIG. 4 (ii) to (vi). That is, the order of different-sized 3-dimensional structures arranged in the probe 113 determines the order of block signals having different levels in electric current, and each of the different-sized 3-dimensional structures and each of the block signals correspond one-to-one with each other. Thus, from the information concerning the order of observed block signals having different levels, the type of probe 113 bound to the DNA sequence that has passed through the nanopore can be identified, which means that the type of specific DNA sequence that has passed through the nanopore can be identified. As described above, it becomes possible to identify the specific DNA sequence in an aqueous solution, to count the number of the specific DNA sequence, and to verify whether the specific DNA sequence is present or not.

<Conventional Method for Detecting Specific DNA Sequence>

Figure 5:
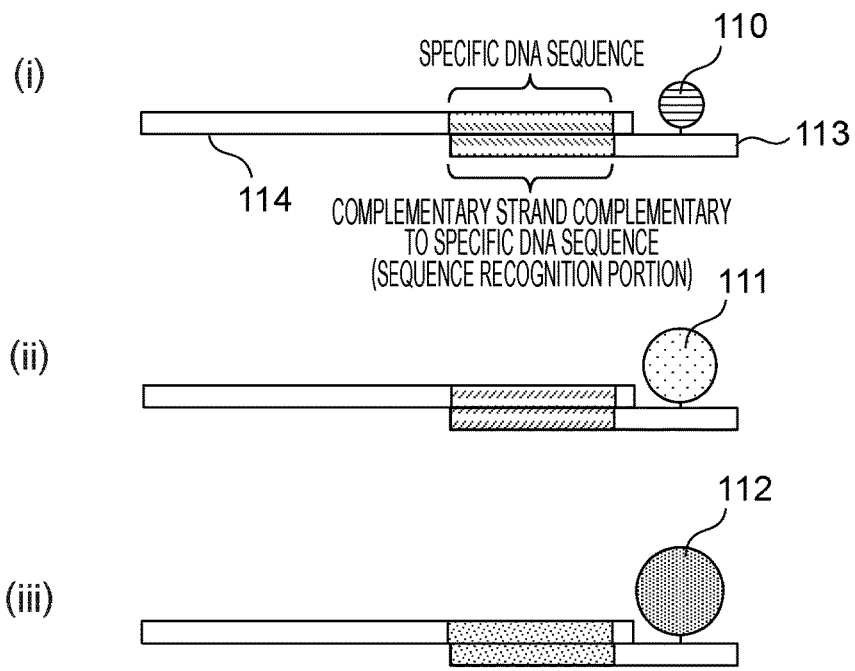
FIG. 5 shows illustrations and graphs for describing a conventional method for detecting a specific DNA sequence.
Figure 5:
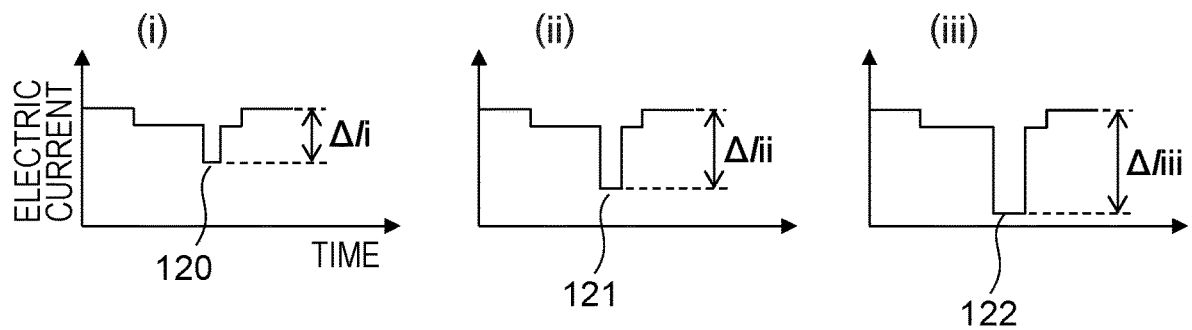
Figure 5:
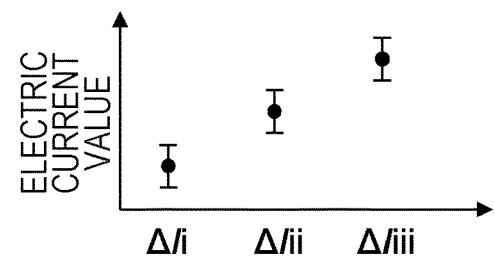

Here, comparison with a conventional method for detecting a specific DNA sequence (conventional method) is performed. FIG. 5 shows illustrations and graphs for describing a conventional method for detecting a specific DNA sequence.

The conventional method includes, when n types of specific DNA sequences to be detected are present, providing n types of probes 113 having different sizes and each having capability to specifically bind to each of the specific DNA sequences, allowing each of the probes to specifically bind to each of the specific DNA sequences, allowing each of the resulting conjugated materials to passes through a nanopore 100, and identifying the types of the specific DNA sequences (DNA fragments 114) that have passed through the nanopore 100 based on the differences in extent of decrease in ionic current that occurs when each of the conjugated material passes through the nanopore. The relationship between the probe 113 and the specific DNA sequence (DNA fragment 114) in this method is as described in the following drawings. That is, when the relationships between probes 113 and specific DNA sequences (DNA fragments 114) are illustrated, as shown in FIG. 5, a probe 113 containing one 3-dimensional structure is bound to one specific DNA sequence (DNA fragment 114) at a sequence recognition portion. In addition, to each of the different specific DNA sequences (DNA fragments 114), each of the probes 113 containing different-sized 3-dimensional structures 110 to 112 is bound. In this case, as shown in FIG. 5, electric current that is produced when the conjugated material, in which the probe 113 and the specific DNA sequence (DNA fragment 114) are bound to each other, passes through the nanopore 100. The electric current changes depending on the size of the 3-dimensional structure. Specifically, as shown in FIG. 5 (i), when a specific DNA sequence (DNA fragment 114) to which a probe 113 containing the smallest 3-dimensional structure 110 is bound passes through a nanopore 100, the smallest block signal 120 derived from the 3-dimensional structure 110 is obtained. Similarly, as shown in FIG. 5 (ii) and (iii), block signals 121 and 122 derived from the 3-dimensional structure 111 and 112, respectively, are obtained. Each of the levels of the block signals reflects the size of each of the 3-dimensional structures 110 to 112. Here, as described above, the extent of decrease in ionic current $\Delta I$ when a certain target substance passes through a nanopore can be represented by $\Delta I = \Delta I_{ave.} \pm \Delta I_{dev.}$, and the value includes a deviation $\Delta I_{dev.}$. Thus, the levels of block signals 120, 121, and 122 (i.e., $\Delta$Ii, $\Delta$Iii, and $\Delta$Iiii) have deviations. Therefore, to ensure a sufficient accuracy in identification of a specific DNA sequence that passes through the nanopore 100, it is required that the $\Delta$I values including the deviations are separated from each other. To achieve this, it is required that differences in size among 3-dimensional structures contained in different probes are sufficiently large.

For example, in an example shown in FIG. 5, a case in which $\Delta I$ values including deviations are represented by $\Delta$Ii=1.5x±x, $\Delta$Iii=4x±x, and $\Delta$Iiii=6.5x±x, respectively, and electric current that flows through a nanopore when there is no detection target substance in the nanopore is about 7.5x is considered. In this case, the $\Delta$Ii, $\Delta$Iii, and $\Delta$Iiii do not overlap each other even including deviations (In a graph at the bottom right of FIG. 5, $\Delta I_{ave.}$ and $\Delta I_{dev.}$ of each of the $\Delta$Ii, $\Delta$Iii, and $\Delta$Iiii are represented by a point and an error bar, respectively. As shown in the graph, the electric current values do not overlap each other.). Thus, the type of a specific DNA sequence with a probe can be accurately identified.

Figure 6:
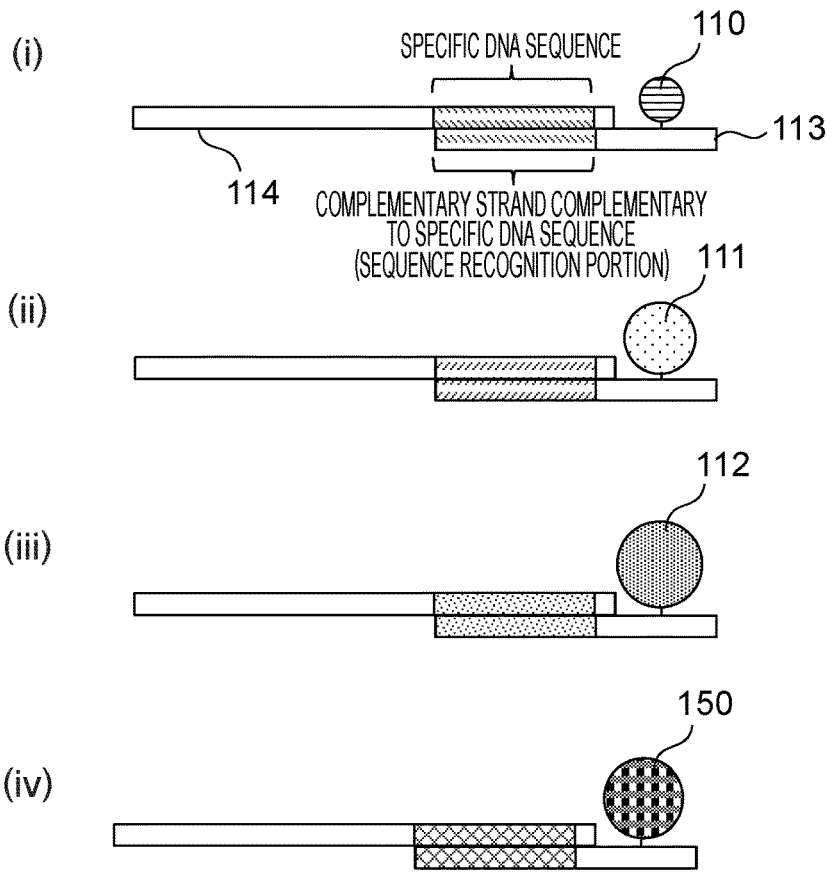
FIG. 6 shows illustrations for describing a fourth probe that can specifically bind to a specific DNA sequence (fourth new specific DNA sequence) other than the three types of specific DNA sequences shown in examples in FIG. 5, and graphs for describing electric current value corresponding to the probe.
Figure 6:
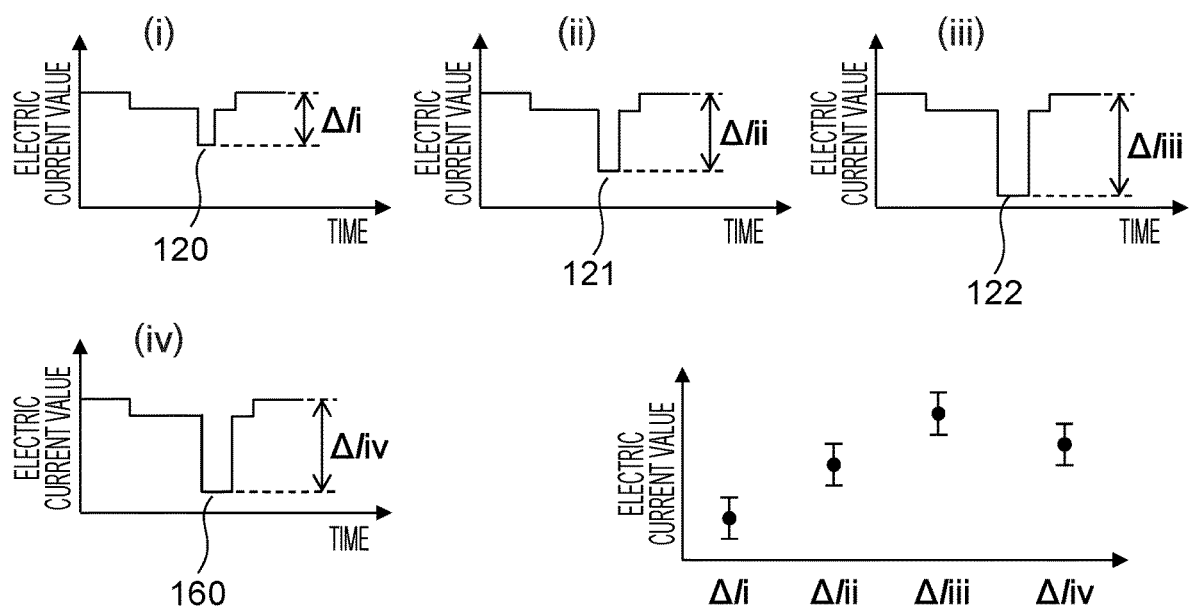

Next, using FIG. 6, a case in which, to identify a specific DNA sequence (DNA fragment 114) other than the three types of specific DNA sequences in the example shown in FIG. 5, that is, an additional fourth specific DNA sequence (DNA fragment 114), a fourth probe that can specifically bind to the fourth specific DNA sequence is provided in a conventional method is considered.

The fourth probe 113 has a 3-dimensional structure 150, and it is required that the 3-dimensional structure 150 has, of course, a size that is different from any of the sizes of 3-dimensional structures 110, 111, and 112 and can pass through a nanopore 100. It is assumed that the probe 113 containing the 3-dimensional structure 150 that satisfies the above-described requirement is bound to the fourth specific DNA sequence to form a conjugated material, and that decrease in electric current $\Delta$Iiv when the conjugated material passes through the nanopore 100 is represented by $\Delta$Iiv=5.3x±x. In this case, the values of $\Delta$Iii, $\Delta$Iiii, and $\Delta$Iiv partly overlap each other in consideration of deviations (see a graph at the bottom right of FIG. 6 showing the $\Delta$I values with error bars). Then, it becomes difficult to precisely make a distinction between an event in which a specific DNA sequence (DNA fragment 114) to which the probe 113 containing the 3-dimensional structure 111 is bound passes through a nanopore and an event in which a specific DNA sequence to which the probe containing the 3-dimensional structure 150 is bound passes through the nanopore based on $\Delta$I values. That is, accuracy in identification decreases. In addition, accuracy in distinction also decreases between an event in which a specific DNA sequence to which the probe 113 containing the 3-dimensional structure 150 is bound passes through the nanopore, and an event in which a specific DNA sequence (DNA fragment 114) to which the probe 113 containing the 3-dimensional structure 112 is bound passes through the nanopore.

As described above, even if a part of the distributions of values of $\Delta$Ii, $\Delta$Iii, $\Delta$Iiii, and $\Delta$Iiv including deviations largely overlap each other even though the size and structure of the 3-dimensional structure 150 contained in the fourth probe 113 is designed in any way, it is difficult to identify four types of specific DNA sequences (DNA fragments 114) with sufficient accuracy. Thus, in this case, as shown in FIG. 5, specific DNA sequences can be identified with sufficient accuracy only when types of the specific DNA sequences (DNA fragment 114) are three or less.

Figure 7:
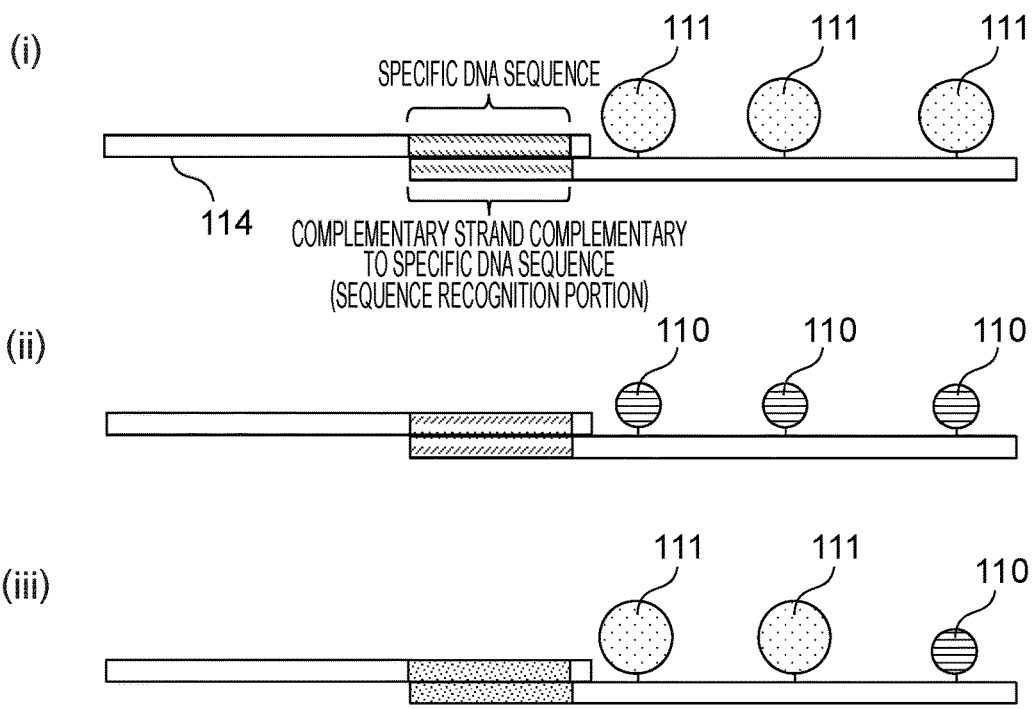
FIG. 7 shows illustrations each showing a case (an example) in which the whole or a part of a plurality of 3-dimensional structures in a probe are constituted by a single type of 3-dimensional structure, and corresponding graphs.
Figure 7:
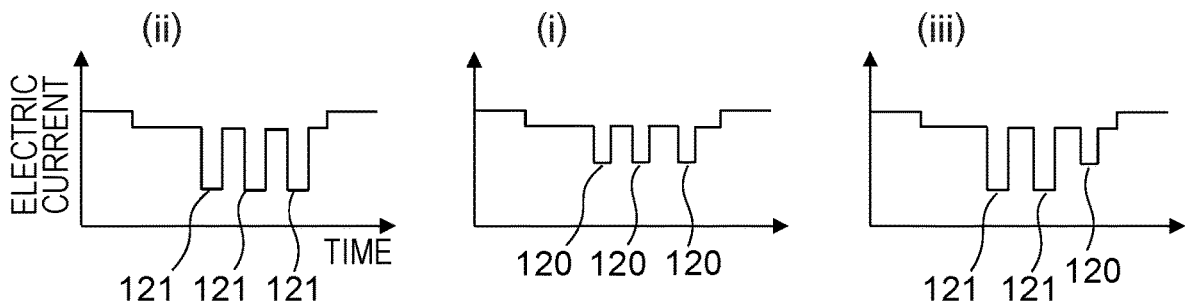

On the other hand, as described above, according to the technique of the present embodiment, accurate detection of more than three types of specific DNA sequences (DNA fragments 114) becomes possible. According to the present embodiment, in the example shown in FIG. 5, using three types of 3-dimensional structures 110, 111, and 112, accurate detection of more than three types of specific DNA sequences (DNA fragments 114) is possible. Characteristics of the method include the following. First, as shown in FIGS. 2 to 4, each one of probes 113 has a structure in which a plurality of 3-dimensional structures (110, 111, and 112) are arranged in the probe, and the order of the 3-dimensional structures arranged in the probe varies depending on the type of the specific DNA sequence (DNA fragment 114). Next, when a conjugated material in which each of the specific DNA sequences (DNA fragment 114) is bound to each of the probes 113 passes through a nanopore 100, based on the order of observed block signals ($\Delta$Ii, $\Delta$Iii, and $\Delta$Iiii) each corresponding to the size of each 3-dimensional structure, the type of the specific DNA sequence (DNA fragment 114) is identified. Since, as described above, the values of $\Delta$Ii, $\Delta$Iii, and $\Delta$Iiii do not overlap each other even including deviations, the order of the observed block signals having sizes of $\Delta$Ii, $\Delta$Iii, and $\Delta$Iiii can be accurately determined. Thus, even when there are only three types of different-sized 3-dimensional structures, for example, six types of specific DNA sequences (DNA fragments 114) can be identified as in FIG. 4. Theoretically, since 27 types of arrangements of three types of different-sized 3-dimensional structures are possible (i.e., 3×3×3=27), 27 types of specific DNA sequences (DNA fragments 114) can be identified. In some cases, all of or a part of the plurality of 3-dimensional structures in a probe 113 may be constituted by the same 3-dimensional structure (some examples are shown in FIG. 7). In these cases, a part or all of a plurality of block signals each derived from the 3-dimensional structure are the same. However, such cases do not affect the accuracy of identification of the specific DNA sequence or counting of the number of the specific DNA sequences (DNA fragments 114). That is, electric current signals of the three examples shown in FIG. 7 can be distinguished from each other, and the electric current signals of the three examples shown in FIG. 7 can be distinguished from electric current signals as shown in FIG. 4.

In addition, it is needless to say that although FIGS. 2 to 4 show examples in which 3 types of 3-dimensional structures are arranged in each probe, the number of types of 3-dimensional structures are not limited to three types. The 3-dimensional structures may be two types or four or more types as long as block signals ($\Delta$I) each derived from a different 3-dimensional structure can be distinguished from each other. In addition, identification of a specific DNA sequence (DNA fragment 114) may be performed as follows. Both a probe 113 in which a plurality of 3-dimensional structures are arranged as shown in FIG. 3 and a probe 113 containing a single 3-dimensional structure as shown in FIG. 5 are used, each of the probes is allowed to recognize and bind to a different specific DNA sequence (DNA fragment 114) to form a conjugated material, and the resulting conjugated material is allowed to pass through a nanopore 100 to identify the specific DNA sequence (DNA fragment 114).

Figure 8:
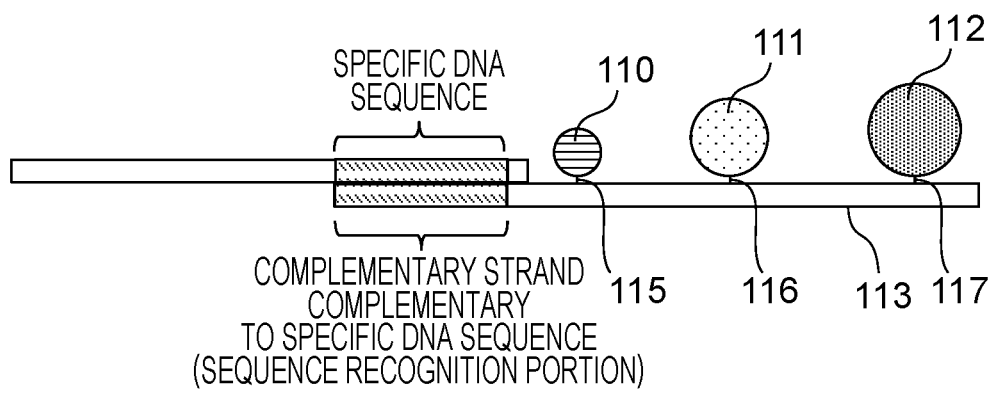
FIG. 8 is an illustration showing an example of a probe containing a plurality of different-sized 3-dimensional structures arranged therein.

FIG. 8 is an illustration showing an example of a probe containing a plurality of different-sized 3-dimensional structures arranged therein. The probe containing a plurality of different-sized 3-dimensional structures arranged therein can be formed, for example, as follows. First, as shown in FIG. 8, DIG 115, an amino group 116, and biotin 117 are provided on a probe (DNA strand) 113 as scaffold molecules, and then a DIG antibody 110, PEG 111, and streptavidin 112, which are capable of specifically binding to the DIG 115, the amino group 116, and the biotin 117, respectively, are bound to the DIG 115, the amino group 116, and the biotin 117, respectively, to form the probe. Of course, the probe using the above-described scaffold molecules and 3-dimensional structures are for illustrative purpose only, and there are a lot of types and combinations of scaffold molecules and 3-dimensional structures. Optimum scaffold molecules and 3-dimensional structures may be used according to conditions to perform the present embodiment (e.g., conditions of a solution).

<Example of Probe Containing Bulge Structure>

Figure 9:
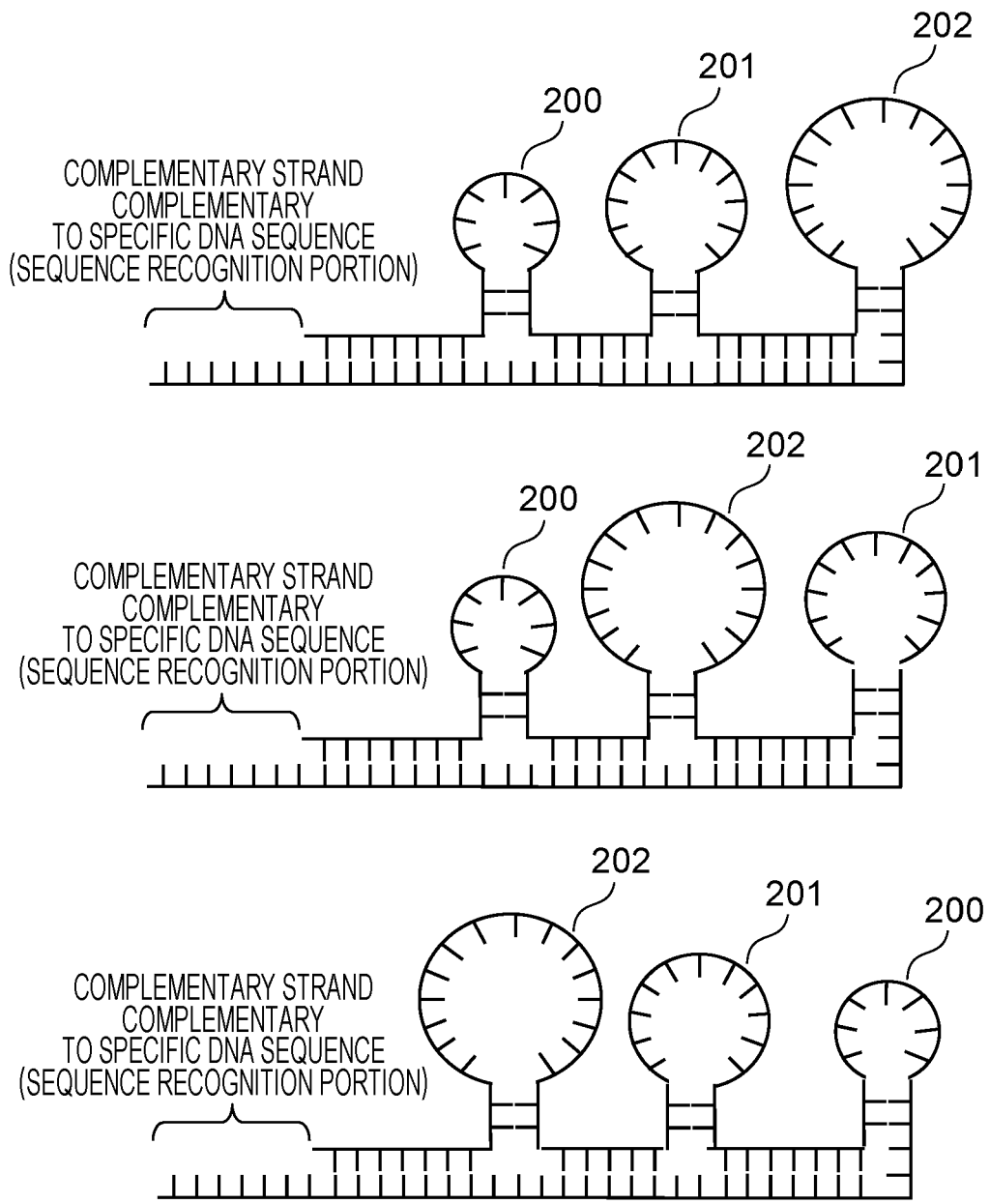
FIG. 9 shows illustrations each showing a structural example of a probe containing bulge structures.

FIG. 9 shows illustrations each showing a structural example of a probe containing bulge structures. The probe may have a structure, as shown in FIG. 9, that includes a double-stranded DNA strand downstream from an end of a sequence recognition portion (complementary strand that is complementary to a specific DNA sequence). The double-stranded DNA strand involves a plurality of portions each having a bulged DNA structure (e.g., bulge-structured DNAs 200, 201, and 202), in which the bulged DNA structures have sizes that are different from each other. The bulged DNA structures correspond to 3-dimensional structures in the description provided above.

Thus, a specific DNA sequence that has passed through a nanopore 100 can be identified as follows. Probes containing different-sized bulged DNA structures, which are arranged in a different order corresponding to the type of a specific DNA sequence to be detected, are provided, each of the probes is allowed to bind to the specific DNA sequence to form a conjugated material, the conjugated material is allowed to pass through a nanopore 100. From information appeared in electric current values concerning the size and the order of block signals observed when the conjugated material passes through the nanopore 100, it is possible to identify the specific DNA sequence that has passed through the nanopore 100.

It should be noted that, in the following embodiments, the words "probe containing 3-dimensional structures" includes both a probe containing 3-dimensional structures constituted by molecules that are different from DNA, such as a DIG antibody 110, PEG 111, and streptavidin 112, and a probe containing 3-dimensional structures that are constituted by bulged DNA structures.

In addition, the description of the present embodiment basically provides an explanation that when the sizes of 3-dimensional structures are different from each other, levels of block signals observed when the 3-dimensional structures pass through a nanopore 100 are different from each other. However, even if the sizes of 3-dimensional structures are almost the same, when the 3-dimensional structures have different physical properties such as electronegativities, levels of block signals observed when the 3-dimensional structures pass through a nanopore are significantly different from each other. That is, even if there are no difference in size, when levels of block signals observed when the 3-dimensional structures pass through a nanopore are different from each other, the 3-dimensional structures can be used as different-sized 3-dimensional structures.

<Example of Specific Technical Effect>

FIG. 14 shows illustrations and graphs for describing an example of a technical effect of a constitution of a specific DNA sequence with a probe according to the present embodiment.

Figure 14A:
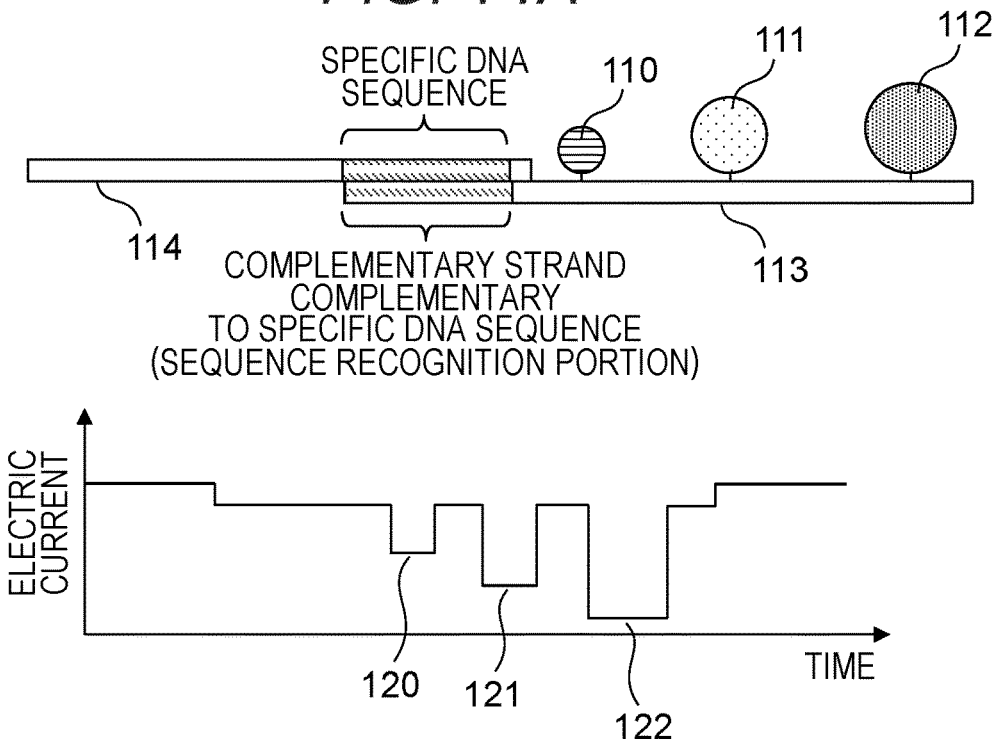
FIGS. 14A to 14B show illustrations and graphs for describing an example of a technical effect of a constitution of a specific DNA sequence with a probe.

As shown in FIG. 14A, when positions of 3-dimensional structures 110, 111, and 112 in a probe 113 are sufficiently separated from each other, block signals each observed when each of the 3-dimensional structures passes through a nanopore 100 are separated from each other. That is, three block signals are observed separately.

Figure 14B:
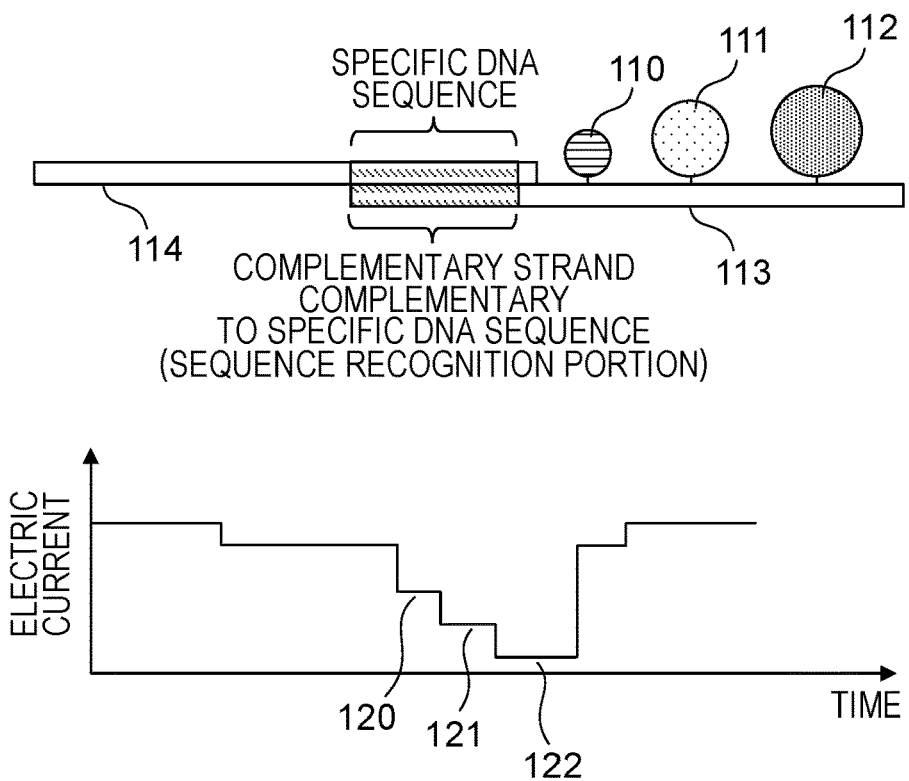

On the other hand, when positions of 3-dimensional structures 110, 111, and 112 in a probe 113 are relatively close to each other, as shown in FIG. 14B, block signals are not separated from each other and form a signal. Even in this case, the electric current value of each of the stairstep signals can be considered as a block signal value, and the electric current values surely reflect the occurrence and the order of passages of the 3-dimensional structures through a nanopore.

Thus, in the same manner as in the methods described in the above embodiments, from information concerning levels and the order of block electric current values each derived from each of the 3-dimensional structures, each specific DNA sequence to which each probe is bound can be identified.

(2) Second Embodiment

The first embodiment describes an example in which a specific DNA sequence (DNA fragment 114) is detected by using a probe 113 having a structure in which a plurality of different-sized 3-dimensional structures are arranged is described. A second embodiment provides an example in which a specific DNA sequence is detected by using a probe containing only single-type and same-sized 3-dimensional structures arranged therein.

Figure 10:
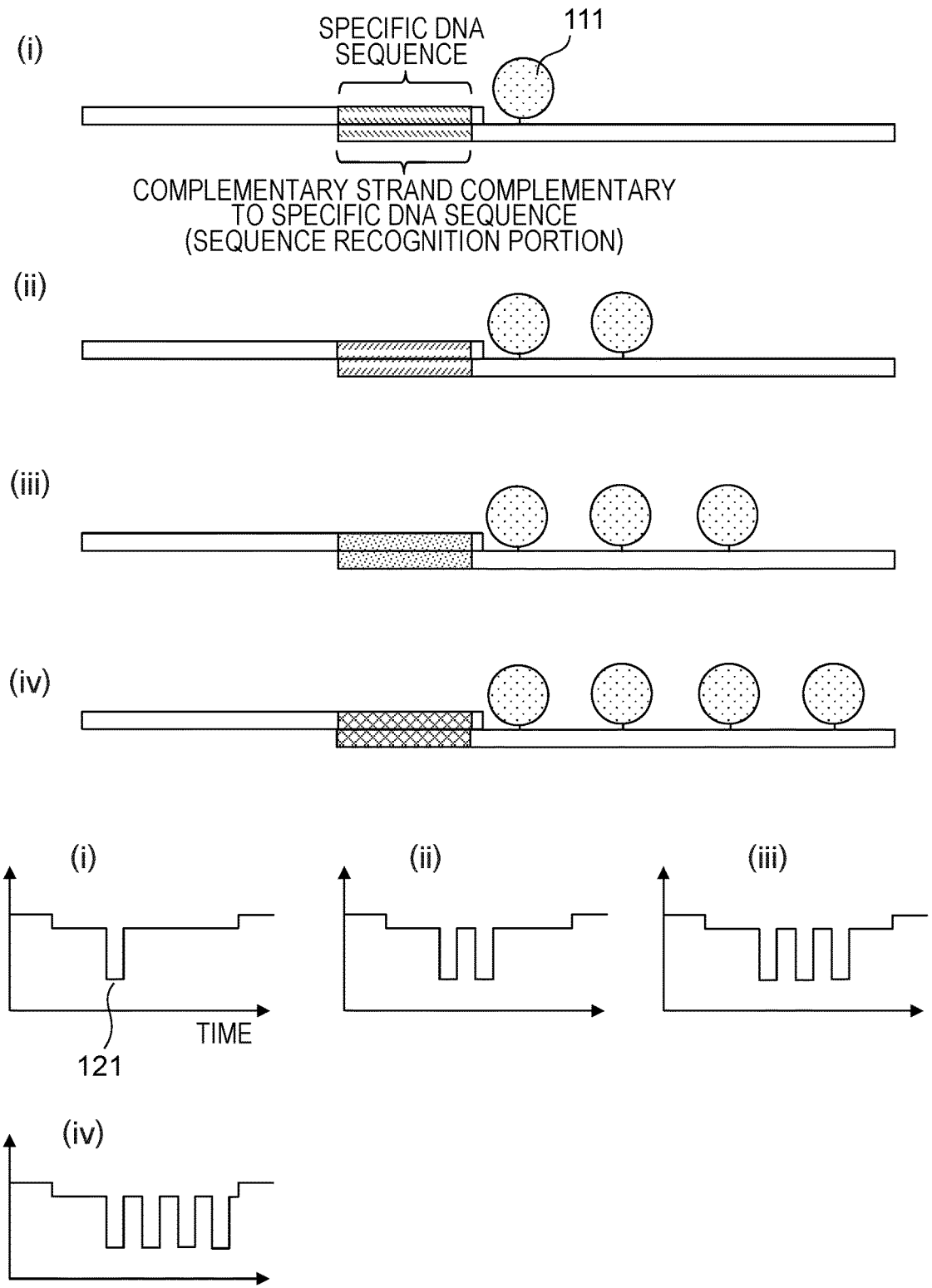
FIG. 10 shows illustrations each showing an exemplary conjugated material in which each of the following four probes is bound to each of specific DNA sequences, the four probes each containing only one, two, three, or four 3-dimensional structures 111 arranged downstream of a sequence recognition portion that recognizes the specific DNA sequence, and corresponding graphs.

As shown in FIG. 10, four types of probes, each of which includes only one, two, three, or four 3-dimensional structures 111 each arranged downstream of a sequence recognition portion that recognizes a specific DNA sequence, are provided, and each of the probes is bound to each specific DNA sequence. When electric current values are measured when each of the conjugated materials of the specific DNA sequences and the probes passes through a nanopore 100, electric current-time wave curves as shown in FIG. 10 (i) to (iv) are obtained. That is, when different types of probes, each of which is bound to a different type of specific DNA sequence, pass through a nanopore 100, the numbers of block signals 121 observed are different from each other. From information concerning the number of block signals, it is possible to identify the type of the specific DNA sequence that has passed through the nanopore 100.

Trevor J. Morin, et al., PLoS ONE 11(5):e0154426. doi:10.1371/journal.pone.0154426 reports that by using PEG as 3-dimensional structures contained in a probe, and using varying numbers of the PEG, it is possible to change the extent of decrease in ionic current (block signal) when DNA with the probe passes through a nanopore. Trevor J. Morin, et al., PLoS ONE 11(5):e0154426. doi:10.1371/journal.pone.0154426 reports, as an example, comparison between a case in which a probe has one PEG structure and a case in which a probe has three PEG structures. In this case, a signal that is produced when DNA to which a probe containing three PEG structures is bound passes through a nanopore is stronger than a signal that is produced when DNA to which a probe containing one PEG structure is bound passes through the nanopore. However, since there are little spaces between the three PEG structures arranged in the probe, the block signal produced when the DNA to which a probe containing three PEG structures is bound passes through a nanopore is observed as a single block signal. On the other hand, as shown in FIG. 10, in the present embodiment, passages of a plurality of 3-dimensional structures through a nanopore are observed as a plurality of independent block signals. In Trevor J. Morin, et al., PLoS ONE 11(5):e0154426. doi:10.1371/journal.pone.0154426, a plurality of 3-dimensional structures are arranged at almost the same position in the probe. In a case in which the probe passes through a nanopore, when a block signal derived from the plurality of 3-dimensional structures is observed as a single block signal, the level of the block signal varies considerably. This is because when the plurality of 3-dimensional structures almost simultaneously enter the nanopore and thereafter almost simultaneously exit the nanopore, the level of the block signal becomes extremely high, and on the other hand, when there is a time lag in entry of the plurality of 3-dimensional structures into the nanopore or there is a time lag in exit of the 3-dimensional structures from the nanopore, the level of the block signal becomes extremely low.

Thus, when the single-type and single-sized 3-dimensional structures are used in a probe, to make a clear difference in pattern of change in ionic current produced when each probe passes through a nanopore 100 by changing the number of the 3-dimensional structures arranged in the probe, it is required, as in the present embodiment shown in FIG. 10, to provide sufficient spaces between the 3-dimensional structures (e.g., the 3-dimensional structures are arranged so as not to interfere with each other, that is, the 3-dimensional structures are arranged so that sufficient distances are maintained to prevent interference when the 3-dimensional structures pass through a nanopore 100). Then, block signals as many as the 3-dimensional structures can be produced. As a result, highly accurate identification of each specific DNA sequence specifically bound to each probe becomes possible.

(3) Third Embodiment

In the first embodiment, cases of FIG. 4 (i) and (iv) are considered. In FIG. 4 (i), when a specific DNA sequence to which a probe is bound enters a nanopore, if a side of the specific DNA sequence portion does not enter a nanopore 100 first, but a side of the 3-dimensional structure 112 enters the nanopore 100 first, the order of block signals produced becomes the following order: 122→121→120. Thus, the manner of change in electric current obtained becomes similar to that in FIG. 4 (iv). Of course, in the case in which the side of 3-dimensional structure 112 enters the nanopore 100 first, as compared to the case in which the side of the specific DNA sequence portion enters the nanopore 100 first, the time from when a conjugated material in which a probe and DNA are bound to each other enters the nanopore 100 and therefore ionic current slightly decreases until when a block signal derived from the first 3-dimensional structure is obtained is different. Thus, it is possible to distinguish, based on the difference in time, whether the DNA with a probe has entered the nanopore 100 from the specific DNA sequence side or has entered from the 3-dimensional structure side. However, since it consumes more treatment procedure, there is possibility that the identification becomes uncertain.

Figure 11:
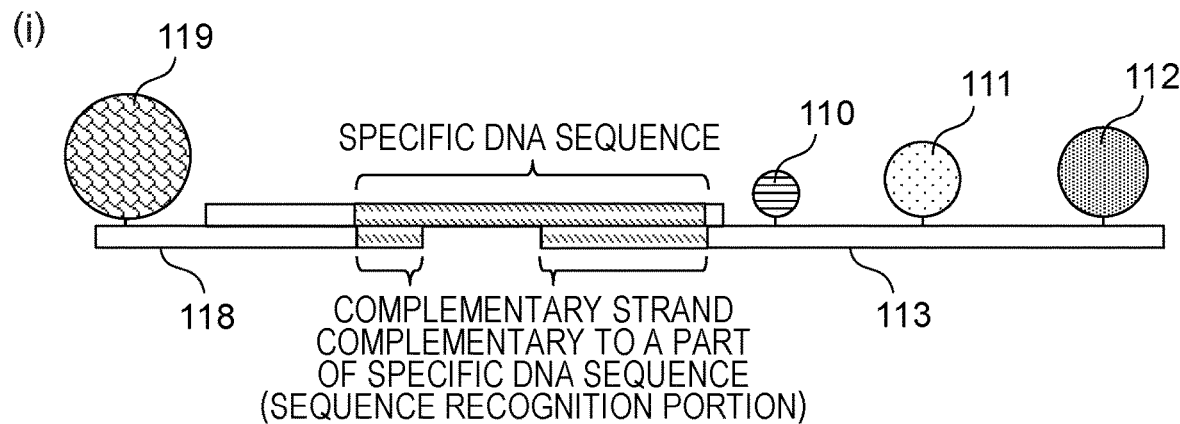
FIG. 11 shows illustrations each showing an example of binding of a probe and a specific DNA sequence in a third embodiment, and corresponding graphs.
Figure 11:
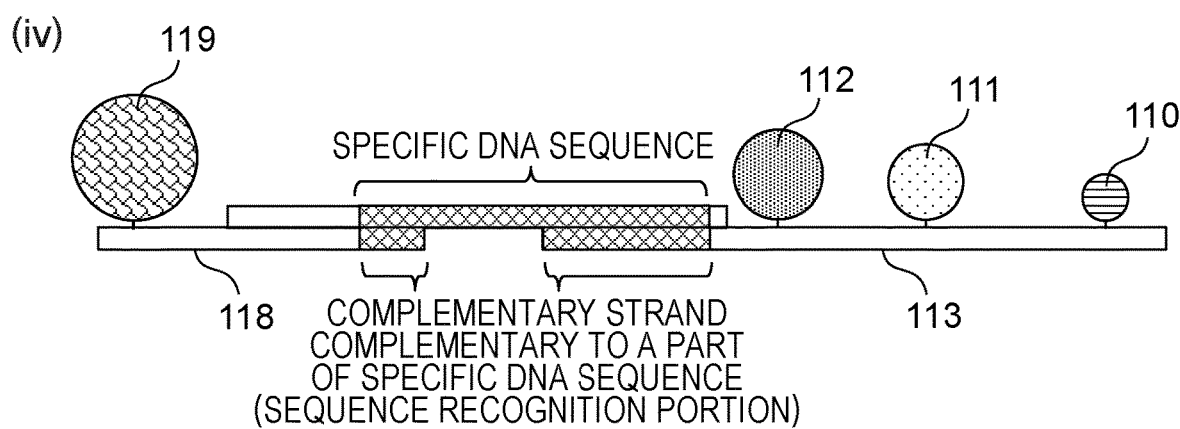
Figure 11:
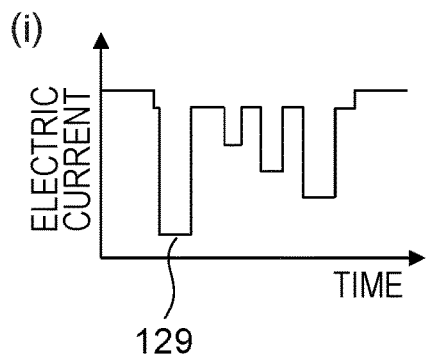
Figure 11:
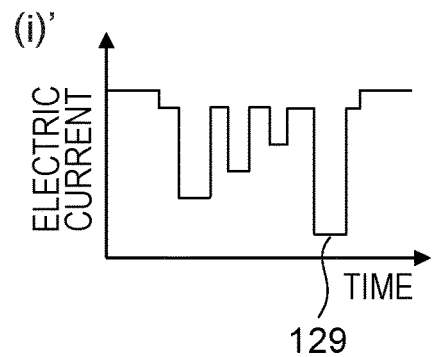
Figure 11:
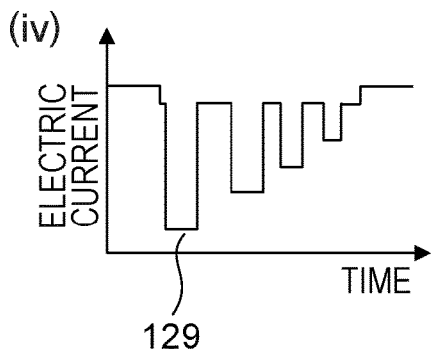
Figure 11:
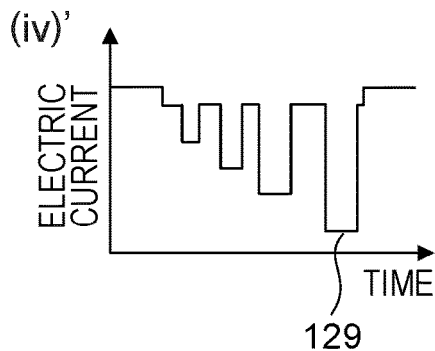

Thus, the third embodiment discloses a method for more securely distinguishing (avoiding confusion) between the cases of FIG. 4 (i) and (iv). FIG. 11 shows illustrations each showing an example of binding of a probe and a specific DNA sequence in the third embodiment, and corresponding graphs. As shown in FIG. 11, a part of each detection target specific DNA sequence is, as in the cases described above, bound to each probe in which different sized 3-dimensional structures are arranged. In addition, in this embodiment, a probe 118 that recognizes a part of each specific DNA sequence that has not bound to a probe 113 is provided. The probe 118 has a 3-dimensional structure 119, and this probe 118 is allowed to bind to the part of the specific DNA sequence. The size of the 3-dimensional structure 119 may be different from the sizes of 3-dimensional structures 110, 111, and 112.

When the resulting conjugated material of a specific DNA sequence and a probe passes through a nanopore, in the case of FIG. 11 (i), corresponding two cases that are a case in which the conjugated material enters the nanopore 100 from the 3-dimensional structure 119 side and a case in which the conjugated material enters the nanopore 100 from the 3-dimensional structure 112 side, two types of electric current wave forms as shown in FIG. 11 (iv) and (iv)' are obtained. On the other hand, in FIG. 11 (iv), corresponding to two cases that are a case in which the conjugated material enters the nanopore 100 from the 3-dimensional structure 119 side and a case in which the conjugated material enters the nanopore 100 from the 3-dimensional structure 110, two types of electric current wave forms as shown in FIG. 11 (iv) and (iv)' are obtained. In each of the wave forms shown in FIG. 11 (i) and (i)', and FIG. 11 (iv) and (iv)', a block signal 129 derived from the 3-dimensional structure 119 is present. Thus, electric current wave forms shown in FIG. 11 (i) and (i)', and electric current wave forms shown in FIG. 11 (iv) and (iv)' are signals that are clearly different from each other. That is, by virtue of the block signal 129, it is possible to clearly determine the end of the two ends of the conjugated material of the specific DNA sequence and the probe from which the conjugated material has entered the nanopore 100. Thus, passage of each of the specific DNA sequences in FIG. 11 (i) and (iv) can be distinguished and identified more accurately.

Here, examples of the 3-dimensional structures used will be provided. Examples of the 3-dimensional structure 110 include a DIG antibody, examples of the 3-dimensional structure 111 include 5-kDa PEG, examples of the 3-dimensional structure 112 include streptavidin, and examples of the 3-dimensional structure 119 include 10-kDa PEG. Next, a scaffold molecule for each of the 3-dimensional structures will be provided. DIG can be used as a scaffold molecule for a DIG antibody, an amino group can be used as a scaffold molecule for PEG, and biotin can be used as a scaffold molecule for streptavidin. For the 3-dimensional structures 110, 111, 112, and 119, different-sized bulge structure DNAs may be used.

(4) Fourth Embodiment

As the amount of a specific DNA sequence in a solution decreases, of course, the frequency of passage of a specific DNA sequence with a probe decreases. Then, it takes an extremely long time until the specific DNA sequence with a probe is detected. In this case, it is possible to amplify (e.g., amplify by PCR reaction) the specific DNA sequence with a probe in advance to increase the amount thereof. FIGS. 12A and 12B, and FIGS. 13A to 13C show illustrations for describing methods each for amplifying a specific DNA sequence with a probe.

Figure 12A:
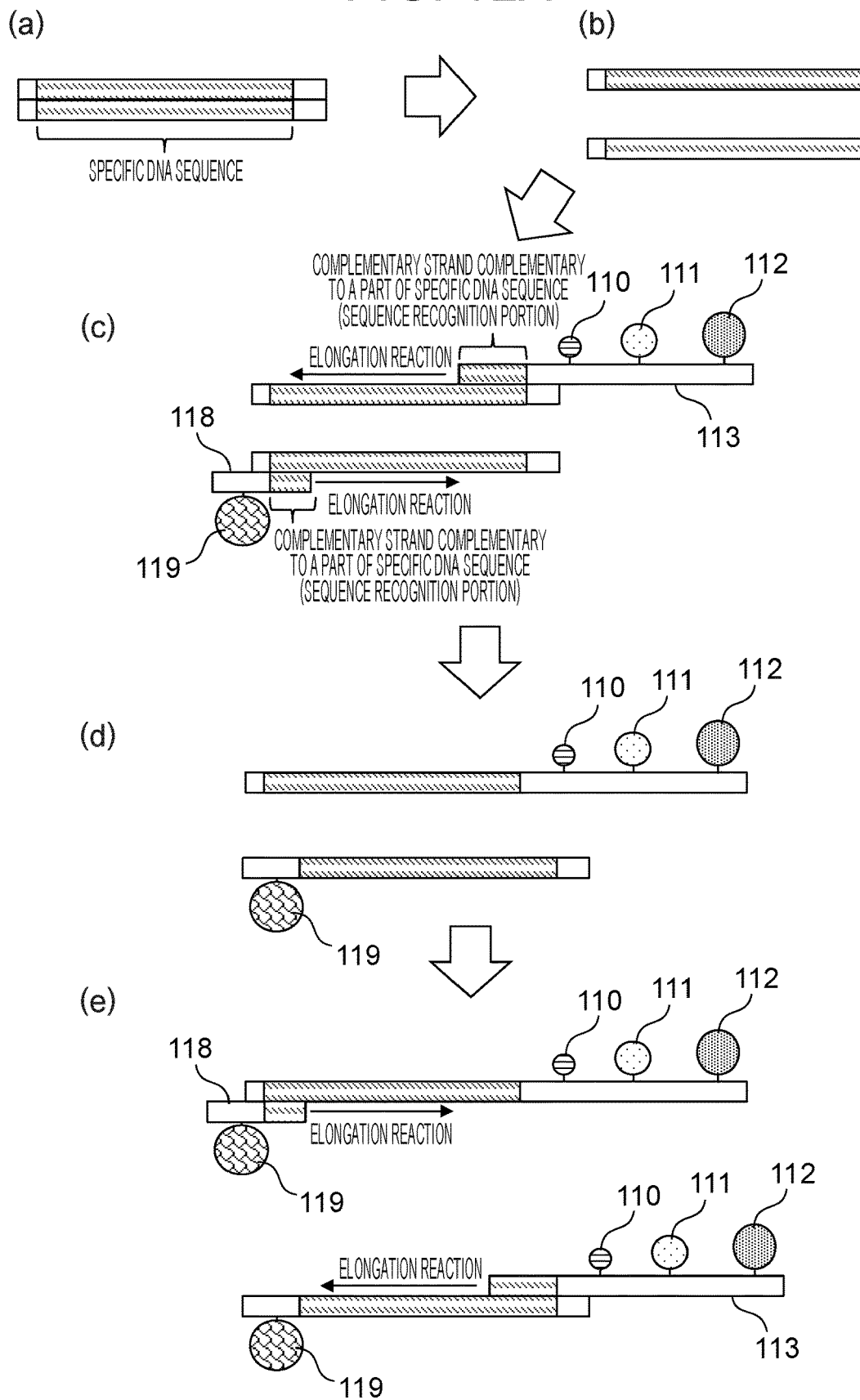
FIGS. 12A and 12B show illustrations for describing a method for amplifying a specific DNA sequence with a probe.
Figure 12B:
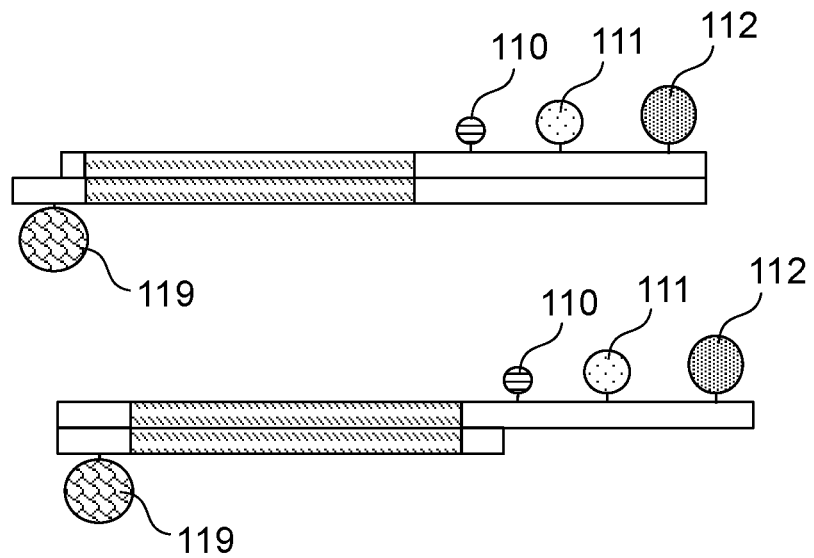
Figure 12B:
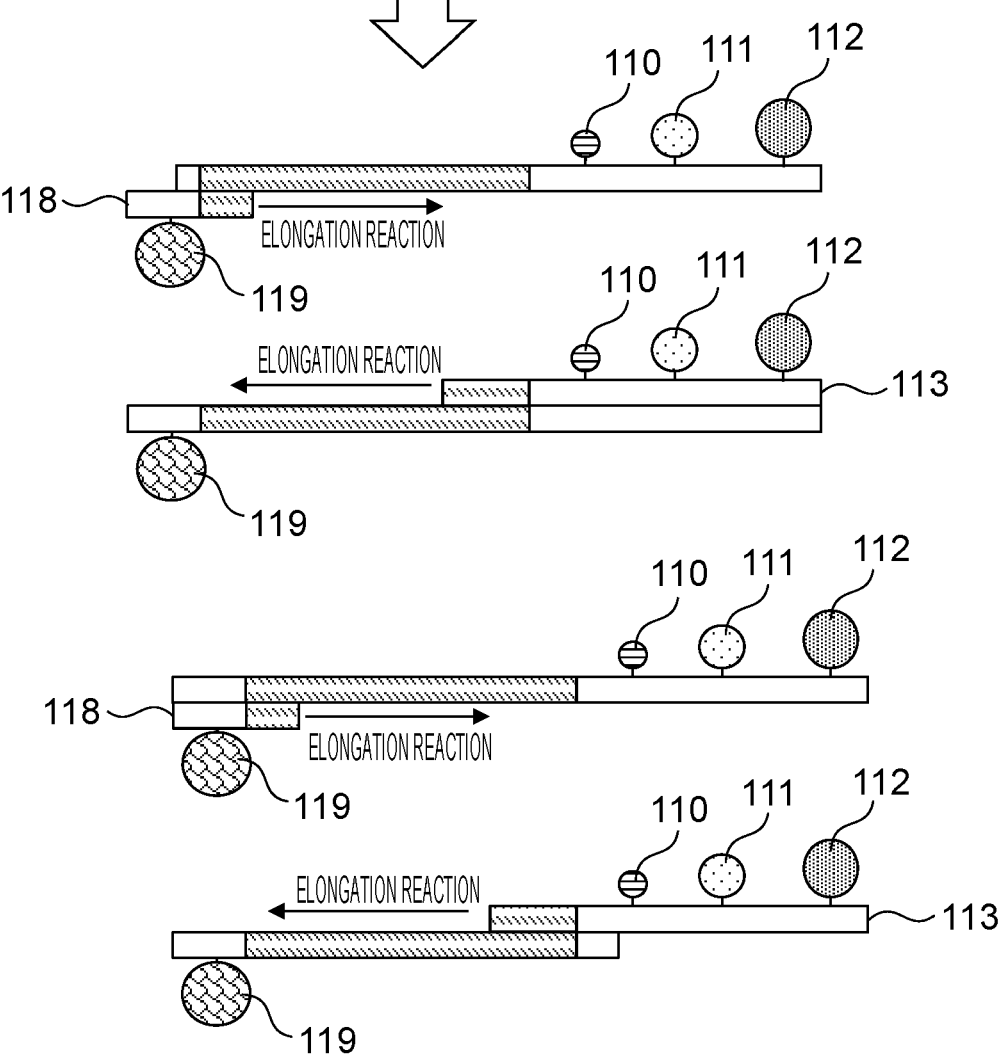

(i) Method Using Probe Containing 3-Dimensional Structure (FIGS. 12A and 12B)

First, a double-stranded DNA strand containing a specific DNA sequence is separated at a high temperature (e.g., 95° C.) to produce single-stranded DNA strands (FIG. 12A (a) to (b)).

Thereafter, a probe 113 and a probe 118 are each allowed to bind to a specific DNA sequence through a sequence recognition portion (FIG. 12A (c)). This reaction is performed at a temperature of, for example, 65° C. Then, the temperature is raised to, for example, 72° C., and, by using the sequence recognition portion in each probe as a primer, a DNA elongation reaction is performed using an enzyme that accelerates the DNA elongation reaction (e.g., a polymerase) and substrates (dNTPs) (FIG. 12A (c)).

After the elongation reaction has been completed, by heating to a temperature of, for example, 95° C., the resulting elongation reaction product is separated into single-stranded DNA strands (FIG. 12A (d)).

Thereafter, the probe 113 and the probe 118 are again allowed to bind to the resulting single-stranded DNA strands through the sequence recognition portions (FIG. 12A (e)). This reaction is performed at a temperature of, for example, 65° C. Then, the temperature is raised to, for example, 72° C., and, by using the sequence recognition portion in each probe as a primer, a DNA elongation reaction is performed using an enzyme that accelerates the DNA elongation reaction (e.g., a polymerase) and substrates (dNTPs) (FIG. 12A (e)).

As a result, products as shown in FIG. 12B (f) are produced. Thereafter, the temperature is raised to, for example, 95° C. to separate the products into single-stranded DNA strands, then the probe 113 and the probe 118 are again allowed to bind to the resulting single-stranded DNA strands through the sequence recognition portion (FIG. 12B (g)). The temperature for annealing is, for example, 65° C. Then, the temperature is raised to, for example, 72° C., and, by using the sequence recognition portion in each probe as a primer, a DNA elongation reaction is performed using an enzyme that accelerates the DNA elongation reaction (e.g., a polymerase) and substrates (dNTPs) (FIG. 12B (g)).

By repeating the above-described procedure, a large amount of the conjugated materials as shown in the first to third embodiments, in each of which a probe containing different-sized 3-dimensional structures arranged therein and a specific DNA sequence are bound to each other, can be obtained. In this case, since the probe already include 3-dimensional structures, the user can use the conjugated material instantly.

Figure 13A:
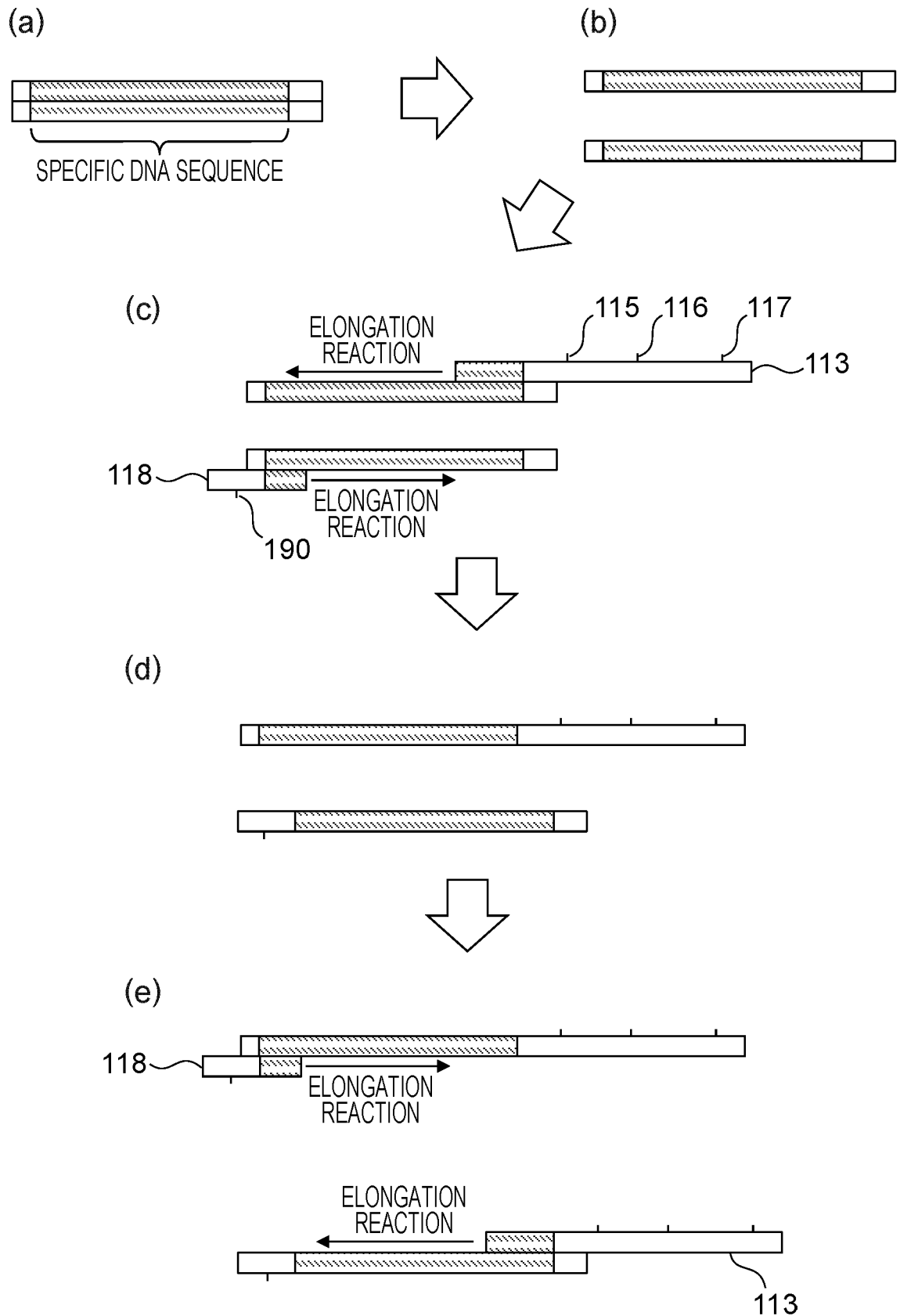
FIGS. 13A to 13C show illustrations for describing a method for amplifying a specific DNA sequence with a probe.
Figure 13B:
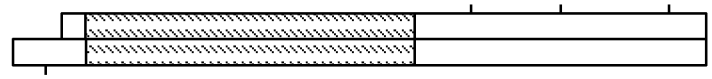
Figure 13B:
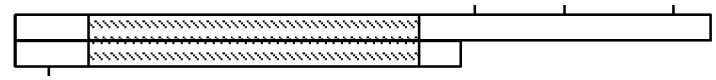
Figure 13B:
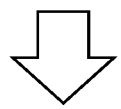
Figure 13B:
Figure 13B:
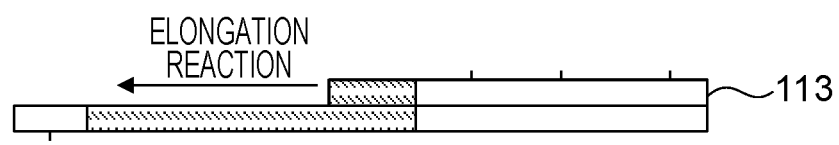
Figure 13B:
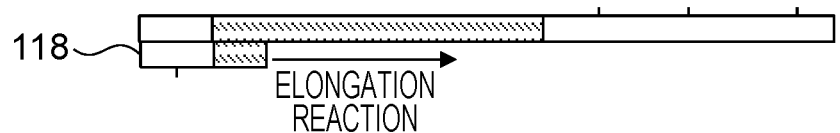
Figure 13B:
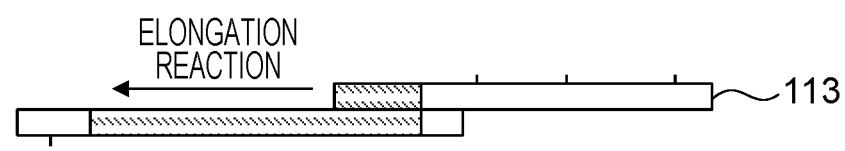
Figure 13C:
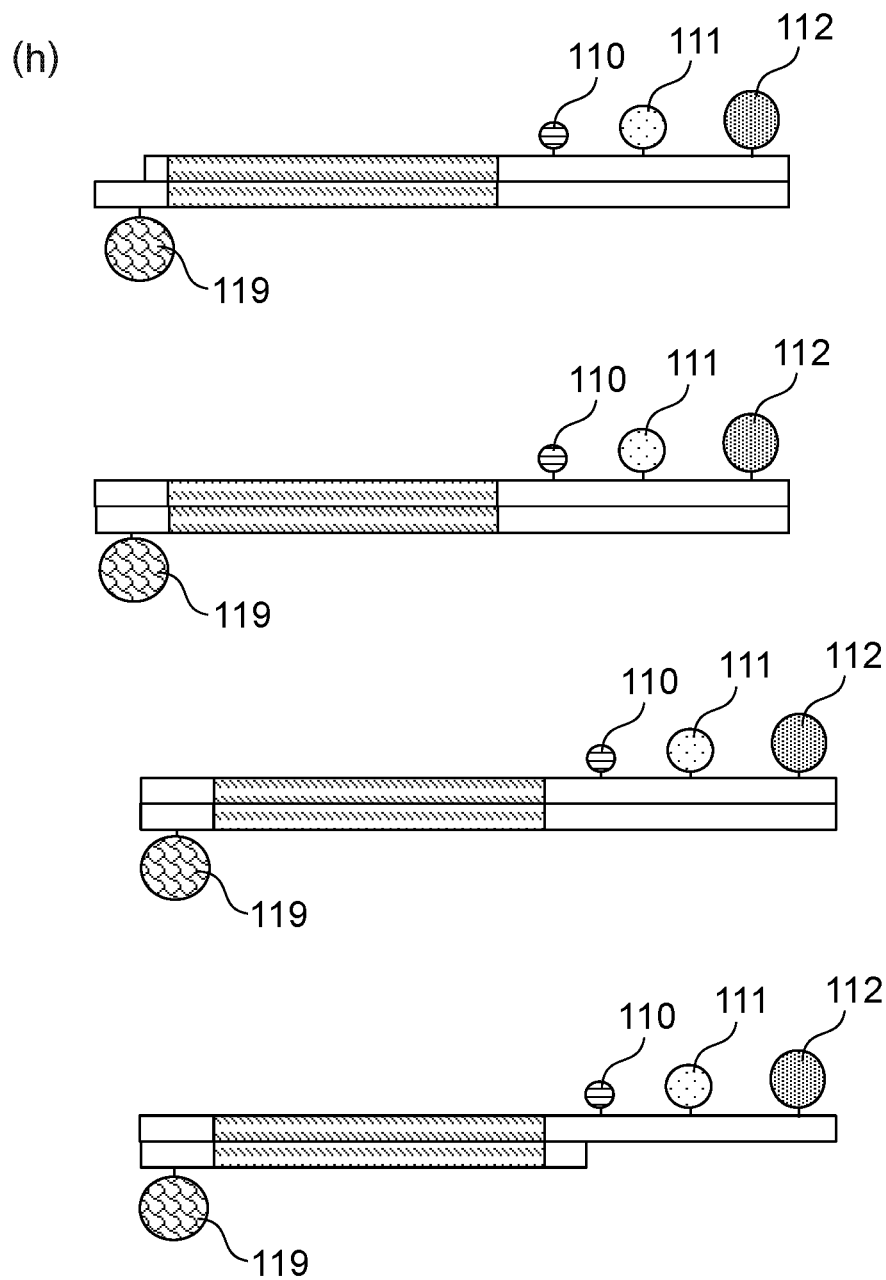

(ii) Method Using Probe Containing Only Scaffold Molecule (FIGS. 13A to 13C)

It is also possible to bind a 3-dimensional structure to a probe 113 after the DNA amplification reaction has been completed. In this case, first, a double-stranded DNA strand including a specific DNA sequence is separated at a high temperature (e.g., 95° C.) into single-stranded DNA strands (FIG. 13A (a) to (b)).

Then, a probe 113 containing scaffold molecules 115, 116, and 117, each of which does not have a 3-dimensional structure, but can specifically bind to a 3-dimensional structure, and a probe 118 containing a scaffold molecule 190 are each allowed to bind to a specific DNA sequence through a sequence recognition portion (FIG. 13A (c)). This reaction is performed at a temperature of, for example, 65° C. Then, the temperature is raised to, for example, 72° C., and, by using the sequence recognition portion in each probe as a primer, a DNA elongation reaction is performed using an enzyme that accelerates the DNA elongation reaction (e.g., a polymerase) and substrates (dNTPs) (FIG. 13A (c)).

After the elongation reaction has been completed, by heating to a temperature of, for example, 95° C., the resulting elongation reaction product is separated into single-stranded DNA strands (FIG. 13A (d)).

The probe 113 and the probe 118 are again allowed to bind to the resulting single-stranded DNA strands through the sequence recognition portions (FIG. 13A (e)). This reaction is performed at a temperature of, for example, 65° C. Then, the temperature is raised to, for example, 72° C., and, by using the sequence recognition portion in each probe as a primer, a DNA elongation reaction is performed using an enzyme that accelerates the DNA elongation reaction (e.g., a polymerase) and substrates (dNTPs) (FIG. 13A (e)).

As a result, products as shown in FIG. 13A (f) are produced. Thereafter, the temperature is raised to, for example, 95° C. to separate the products into single-stranded DNA strands, then the probe 113 and the probe 118 are again allowed to bind to the resulting single-stranded DNA strands through the sequence recognition portion (FIG. 13A (g)). The temperature for annealing is, for example, 65° C. Then, the temperature is raised to, for example, 72° C., and, by using the sequence recognition portion in each probe as a primer, a DNA elongation reaction is performed using an enzyme that accelerates the DNA elongation reaction (e.g., a polymerase) and substrates (dNTPs) (FIG. 13A (g)).

When mixing the product obtained by repeating the above-described procedure and 3-dimensional structures 110, 111, 112, and 119 in a solution, it is possible to obtain a large amount of products as shown in FIG. 13C. That is, by using the above-described procedure, it is possible to obtain a large amount of the conjugated materials as shown in the first to third embodiments, in each of which probes containing different-sized 3-dimensional structures arranged therein and specific DNA sequences are bound to each other. In this case, the user is required to perform the treatment for binding the 3-dimensional structures to the probe 113 after the DNA amplification reaction has been completed, and it is possible to avoid a problem that the 3-dimensional structures are dissociated from the probe by heat treatment during DNA amplification since the 3-dimensional structures are conjugated at the end of the procedure.

(5) Fifth Embodiment

Figure 15:
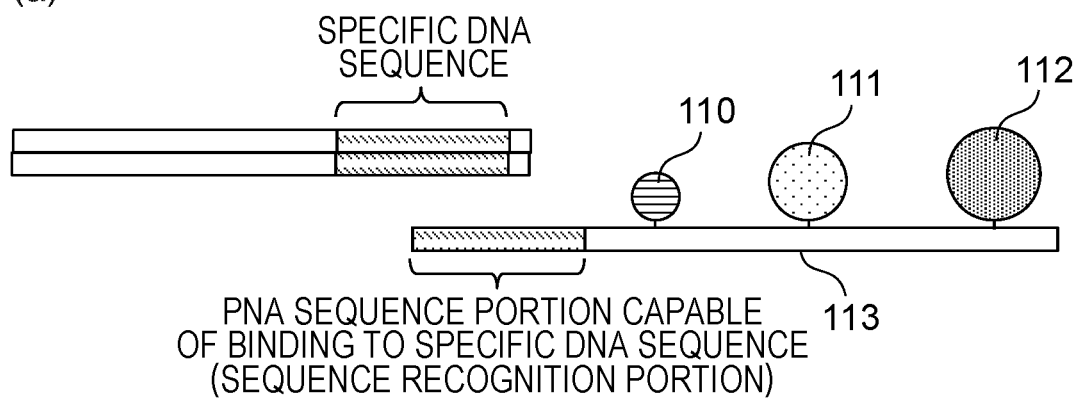
FIG. 15 shows illustrations showing binding of a probe and specific DNA sequences according to a sixth embodiment.
Figure 15:
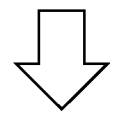
Figure 15:
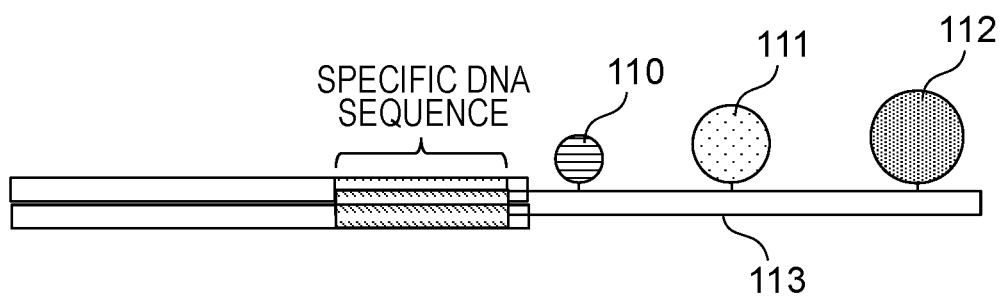
Figure 16:
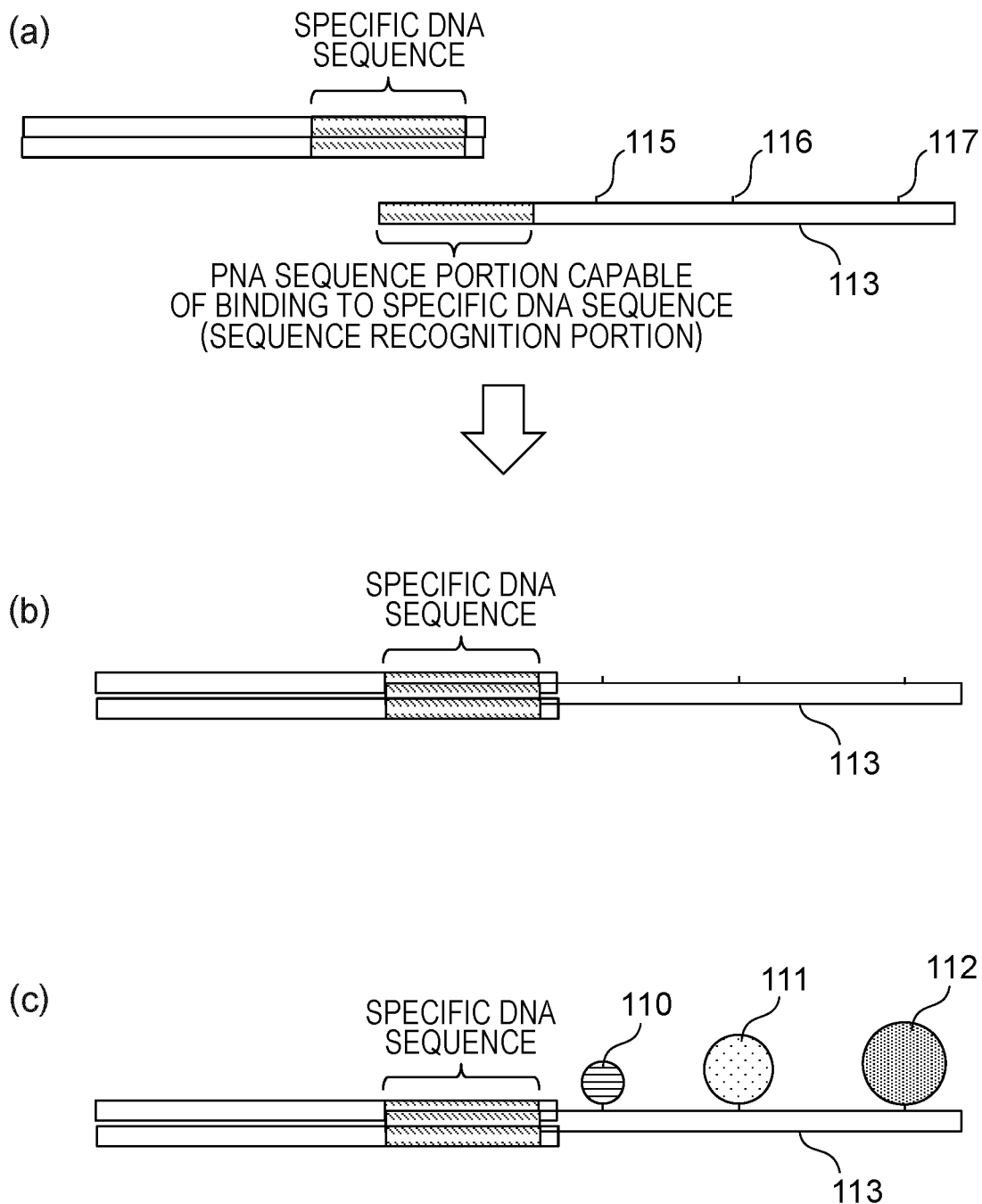
FIG. 16 shows illustrations showing binding of a probe and specific DNA sequences according to a sixth embodiment.

FIGS. 15 and 16 show illustrations each showing binding of a probe and specific DNA sequences according to a fifth embodiment. In each of the first to fourth embodiments, the specific sequence recognition portion present in the probe 113 is a complementary strand that is complementary to the specific DNA sequence. In the fifth embodiment, as shown in FIG. 15 (a), the specific sequence recognition portion present in the probe 113 is constituted by PNA. The PNA portion is designed so as to be capable of specifically binding to the specific DNA sequence portion. In order to allow a probe 113 having the PNA portion as a specific sequence recognition portion to specifically bind to a double-stranded DNA strand having the specific DNA sequence, it is required to heat (e.g., 90° C.) a solution obtained by mixing the double-stranded DNA strand having specific DNA sequences and the probe 113, and thereafter to cool the heated solution. As a result, as shown in FIG. 15 (b), the PNA invades a portion having the specific DNA sequences in the double-stranded DNA strand. Thus, the probe 113 can be specifically bound to the specific DNA sequences.

Here, as shown in FIG. 16, it is also possible to allow the 3-dimensional structures to bind to the probe 113 at the end of the reaction step. In this case, a solution obtained by mixing a double-stranded DNA strand having specific DNA sequences and the probe 113 containing scaffold molecules 115, 116, and 117 having the 3-dimensional structures is heated (e.g., 90° C.), and thereafter cooled. As a result, as shown in FIG. 16 (b), a structure in which a PNA portion has invaded the specific sequence portion can be obtained. Thereafter, the resulting structure and 3-dimensional structures are mixed, and, eventually, as shown in FIG. 16 (c), a probe 113 containing 3-dimensional structures 110, 111, and 112 can be bound to specific DNA sequences.

(6) Summary (i) A probe according to the first embodiment contains, as shown in FIG. 2, a sequence recognition portion (complementary strand that is complementary to a specific DNA sequence) that is capable of specifically binding to a desired DNA sequence, and a probe portion that includes a plurality of 3-dimensional structures arranged downstream from an end of the sequence recognition portion, wherein the plurality of 3-dimensional structures (110, 111, and 112: for example, as the 3-dimensional structures, structures including any of streptavidin, a PEG or DIG antibody, or a bulged DNA structure, or a combination thereof can be used) are arranged in an order so that the order corresponds one-to-one with the DNA sequence. In this case, the plurality of 3-dimensional structure may be different in type from each other, and the number of the 3-dimensional structures may be the same as in other probes. Since the probe is configured as described above, even when the number of types of specific DNA sequences to be detected increases, it is possible to maintain a high accuracy in identification and counting of the number of the specific DNA sequences, or a high accuracy in verification of whether the specific DNA sequence is present or not.

In this case, the method for identification of the desired DNA sequence in a solution includes binding the above-described probe to the DNA sequence at a sequence recognition portion to form a construct, measuring electric current value when the construct in which the probe and the DNA sequence are bound to each other passes through a nanopore, and specifying the order of a plurality of 3-dimensional structures arranged based on a wave form of the electric current value to identify the presence of the DNA sequence. In this case, the wave form of the measured electric current value is a signal that reflects passage of the plurality of constructs.

A plurality of the probes may be collectively provided as a set. Similarly, probes according to other embodiments also may be provided as a set.

(ii) A probe according to the second embodiment includes a sequence recognition portion that is capable of specifically binding to a desired DNA sequence (complementary strand that is complementary to a specific DNA sequence), and a portion that includes a plurality of 3-dimensional structures (111 in FIG. 10) arranged downstream from an end of the sequence recognition portion, in which the plurality of 3-dimensional structures are constituted by only single-type constructs, and the number of the 3-dimensional structures corresponds one-to-one with the DNA sequence. In this case, the plurality of 3-dimensional structures are arranged so that a sufficient distance is maintained from each other to prevent interference when the 3-dimensional structures pass through a nanopore. Since such probes are used, even when single-type of 3-dimensional structures are used, it is possible to maintain a high accuracy in identification and counting of the number of the specific DNA sequences or the like.

In this case, the method for identification of a desired DNA sequence in a solution includes binding the above-described probe (FIG. 10) to the DNA sequence at the above-described sequence recognition portion to a construct, measuring electric current when the construct in which the probe and the DNA sequence are bound to each other passes through a nanopore, and specifying the number of the plurality of 3-dimensional structure arrangements based on a wave form of the electric current to identify the presence of the DNA sequence. In this case, the wave form of the measured electric current is a signal that reflects passage of the plurality of 3-dimensional structures (the number of block signals observed when the 3-dimensional structures have passed a nanopore corresponds to the number of the 3-dimensional structures).

(iii) A probe according to the third embodiment includes, in addition to the constitution in the above-described probe of the first embodiment, a second probe that binds to a DNA sequence at a part of the DNA sequence that is different from the portion to which the probe of the first embodiment binds (FIG. 11: a probe set). Since the probe is configured as described above, the direction of the probe entering a nanopore can be clearly distinguished, and accurate identification of a specific DNA sequence within a short time becomes possible.

(iv) A probe according to the fourth embodiment includes a sequence recognition portion that is capable of specifically binding to a desired DNA sequence, and a first probe portion containing a plurality of scaffold molecules that are each capable of specifically binding to a specific 3-dimensional structure and are arranged downstream from an end of the sequence recognition portion, wherein the plurality of scaffold molecules are arranged in an order so that the order corresponds one-to-one with the DNA sequence. Accordingly, since the 3-dimensional structures can be bound to a probe after a specific DNA sequence with the probe has been amplified, it is possible to avoid a problem that the 3-dimensional structures are dissociated from the probe by the treatment in the amplification.

(v) A probe according to the fifth embodiment is as in the above-described probe in the first embodiment, except that the sequence recognition portion is constituted by PNA. Accordingly, the probe can be bound to the specific sequence portion of a double-stranded DNA strand through the PNA.

(vi) Herein, a suitable combination of a plurality of constituents disclosed in the embodiments can provide various inventions. For example, some constituents can be excluded from the total constituents shown in each embodiment. Alternatively, suitable constituents shown in different embodiments can be used in combination. Although the present disclosure is described above with reference to specific examples, the examples are given for the purpose of illustration, and are not intended to limit the invention in any way.

In addition, those of ordinary skill in the art will appreciate other embodiments of the present disclosure from consideration of specification and embodiments of the present disclosure disclosed herein. Various aspects of the embodiments disclosed herein can be used alone or in any combination. The specification and specific examples are representative of the disclosure, and the scope and spirit of the disclosure are defined by the following claims.

What is claimed is:

1. A method for identifying a DNA sequence in a solution, the method comprising:
    providing a plurality of constructs, in a form of a plurality of different target molecules, each having a probe hybridized thereto;
    for each of the plurality of constructs:
        binding the probe to the DNA sequence at a sequence recognition portion to form a construct of the plurality of constructs, the probe including:
            the sequence recognition portion including a complementary strand sequence that is capable of specifically binding to the DNA sequence; and
            a first probe portion that includes a plurality of 3-dimensional structures arranged downstream from an end of the sequence recognition portion, wherein the plurality of 3-dimensional structures are arranged in an order so that the order corresponds one-to-one with the DNA sequence; and
        measuring electric current when the construct in which the probe and the DNA sequence are bound to each other passes through a nanopore;
    specifying the order of the plurality of 3-dimensional structures arranged based on a wave form of the electric current to identify presence of the DNA sequence, wherein the wave form of the electric current is a signal that reflects passage of the plurality of constructs; and
    identifying each of the plurality of different DNA sequences, using the probe of each of the plurality of constructs such that a number and types of the plurality of 3-dimensional structures in the probe of each of the plurality of constructs are the same, and arrangements of the plurality of 3-dimensional structures in the probe of each of the plurality of constructs are different,
    wherein, according to the arrangements of the plurality of 3-dimensional structures, the sequence recognition portion in the probe of each of the plurality of constructs is different from the sequence recognition portion in the probe of remaining constructs of the plurality of constructs, and
    wherein sizes of the plurality of 3-dimensional structures within the probe of each of the plurality of constructs are different, such that, upon passing through the nanopore, amounts of drop of the electric current in the wave are different for adjacent structures of the plurality of 3-dimensional structures within the probe of each of the plurality of constructs.

2. The method according to claim 1, wherein the wave form of the electric current contains a plurality of block signals, and
    wherein the method comprises identifying the arrangements of the plurality of 3-dimensional structures from information concerning a level of each of the block signals and the order of appearance of each of the block signals.

3. The method according to claim 1, wherein the plurality of 3-dimensional structures in the probe of each of the plurality of constructs are constituted by a bulged DNA structure.

4. The method according to claim 1, wherein the method further comprises binding a specific-binding second probe of each of the plurality of constructs to the DNA sequence at a part of the DNA sequence that is different from a portion to which the sequence recognition portion of the probe of each of the plurality of constructs binds.

5. The method according to claim 1, wherein the sequence recognition portion has a structure of a complementary strand sequence that is complementary to a part of the DNA sequence or all of the DNA sequence.

* * * * *